United States Patent
Osorio

(10) Patent No.: US 12,419,564 B2
(45) Date of Patent: Sep. 23, 2025

(54) SENSOR SYSTEMS IMPLANTABLE AT BONES OF THE FACE OR THE SKULL BASE

(71) Applicant: Flint Hills Scientific, L.L.C., Lawrence, KS (US)

(72) Inventor: Ivan Osorio, Leawood, KS (US)

(73) Assignee: FLINT HILLS SCIENTIFIC, L.L.C., Lawrence, KS (US)

( * ) Notice: Subject to any disclaimer, the term of this patent is extended or adjusted under 35 U.S.C. 154(b) by 1205 days.

(21) Appl. No.: 13/678,339

(22) Filed: Nov. 15, 2012

(65) Prior Publication Data

US 2014/0135589 A1  May 15, 2014

(51) Int. Cl.
| | | |
|---|---|---|
| *A61B 5/00* | (2006.01) | |
| *A61B 5/03* | (2006.01) | |
| *A61B 5/07* | (2006.01) | |
| *A61B 5/369* | (2021.01) | |

(Continued)

(52) U.S. Cl.
CPC .......... *A61B 5/4064* (2013.01); *A61B 5/0031* (2013.01); *A61B 5/031* (2013.01); *A61B 5/369* (2021.01); *A61B 5/6867* (2013.01); *A61B 5/6868* (2013.01); *A61B 5/6879* (2013.01); *A61B 5/6882* (2013.01); *A61B 5/72* (2013.01); *A61N 1/0534* (2013.01); *A61N 1/0539* (2013.01); *A61N 1/36064* (2013.01); *A61B 5/076* (2013.01); *A61B 5/4094* (2013.01); *A61B 2560/063* (2013.01)

(58) Field of Classification Search
CPC ..... A61B 5/0476; A61B 5/4064; A61B 5/031; A61B 5/6867; A61B 5/6879; A61B 5/72; A61B 2560/063; A61B 5/0031; A61B 5/076; A61B 5/4094; A61B 5/6868; A61B 5/6882; A61N 1/375; A61N 1/0534; A61N 1/0539; A61N 1/36064
USPC ............... 600/300, 378, 544; 607/2, 45, 62
See application file for complete search history.

(56) References Cited

U.S. PATENT DOCUMENTS

| | | | | |
|---|---|---|---|---|
| 4,471,786 A | * | 9/1984 | Inagaki ................ | A61B 5/0031 128/903 |
| 4,928,705 A | * | 5/1990 | Sekhar ................... | A61B 7/001 600/586 |

(Continued)

FOREIGN PATENT DOCUMENTS

DE        4341903 A1 *  6/1995  ........... A61B 5/0031

OTHER PUBLICATIONS

JF Thompson et al., Chapter 12 - The Central Nervous System: The Brain and Spinal Cord, 2010 (http://www.apsubiology.org/anatomy/2010/2010_PPts/Chapter%2012%20-%20The%20Brain%20and%20Spinal%20Cord.ppt).*

(Continued)

*Primary Examiner* — Benjamin J Klein
*Assistant Examiner* — Vynn V Huh
(74) *Attorney, Agent, or Firm* — CF 3; Stephen Eisenmann

(57) ABSTRACT

In one embodiment, the present disclosure relates to an implantable sensor system for sensing biological signal of a patient comprising: an anchor for coupling the sensor to at least one patient skull base structure; a first sensor coupled to the anchor for sensing, at a first location proximate to the at least one patient skull base structure, at least one biological signal of a patient; and a transmitter coupled to the sensor and capable of transmitting data from the sensor to an external device.

13 Claims, 16 Drawing Sheets

(51) Int. Cl.
*A61N 1/05* (2006.01)
*A61N 1/36* (2006.01)

(56) References Cited

U.S. PATENT DOCUMENTS

| | | | | |
|---|---|---|---|---|
| 6,298,262 | B1* | 10/2001 | Franck | A61B 90/11 600/426 |
| 6,560,486 | B1* | 5/2003 | Osorio | A61B 5/4094 600/36 |
| 2002/0103512 | A1* | 8/2002 | Echauz | A61B 5/0482 607/9 |
| 2005/0021103 | A1* | 1/2005 | DiLorenzo | A61N 1/3605 607/45 |
| 2006/0020299 | A1* | 1/2006 | Shalev | A61N 1/3605 607/42 |
| 2006/0025704 | A1* | 2/2006 | Stendel | A61B 5/6864 600/561 |
| 2006/0235484 | A1* | 10/2006 | Jaax | A61N 1/36071 607/46 |
| 2006/0293723 | A1* | 12/2006 | Whitehurst | A61M 5/14276 607/48 |
| 2007/0162085 | A1* | 7/2007 | DiLorenzo | A61N 1/36007 607/40 |
| 2007/0167867 | A1* | 7/2007 | Wolf | A61B 5/0031 600/561 |
| 2008/0262319 | A1* | 10/2008 | Reichenberger | A61B 5/6864 600/300 |
| 2009/0143696 | A1* | 6/2009 | Najafi | A61B 5/0031 600/561 |
| 2012/0265028 | A1 | 10/2012 | Hughes et al. | |

OTHER PUBLICATIONS

International Application No. PCT/US2013/067430, "PCT Search Report and Written Opinion" dated Feb. 1, 19, 2014, 11 pgs.

* cited by examiner

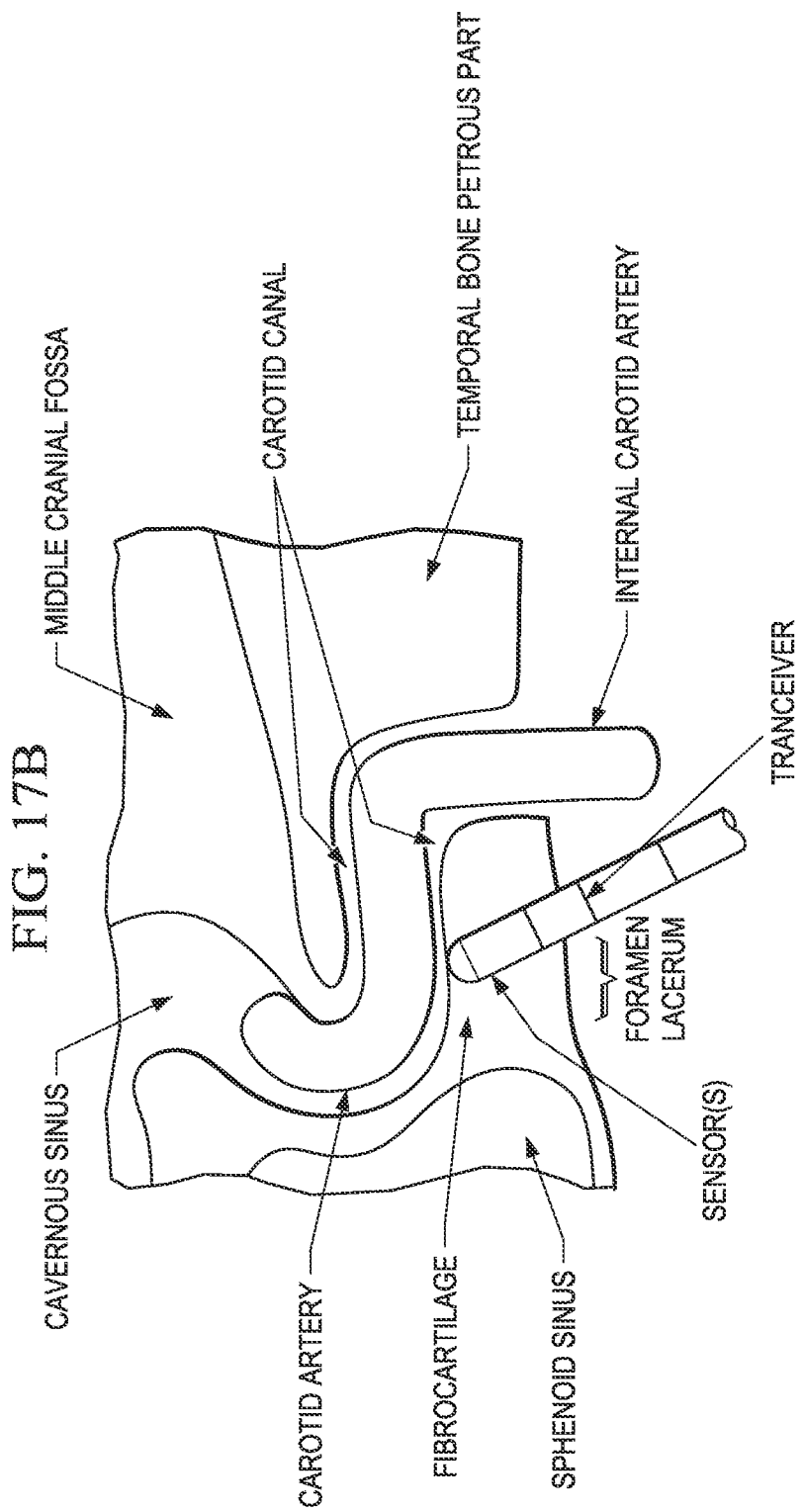

SENSOR SYSTEMS IMPLANTABLE AT BONES OF THE FACE OR THE SKULL BASE

BACKGROUND OF THE INVENTION

1. Field of the Invention

The present disclosure relates generally to the field of sensing biological signals from a human or animal body. More particularly, it concerns sensing biological signals by use of a sensor system having components implantable at a location proximate facial bones, base of the skull bones, or nearby biological structures.

2. Description of Related Art

A variety of electrical, chemical, thermal and other activity constantly occurs in the human brain and its afferent and efferent pathways. Monitoring these activities may be useful in observing and/or treating various medical conditions, such as epilepsy, stroke, degenerative diseases, or tumors. Performing such monitoring in a more efficient and cost-effective, as well as safer and more practical manner than the state of the art, is an ongoing challenge.

The state of the art in monitoring electrical activity in the brain includes electroencephalography (EEG), involving electrodes placed at various locations on the patient's scalp. Though not invasive, EEG only surveys approximately ⅓ of the cortical mantle, and the signals it yields are markedly (10-60 times) and differentially attenuated, as well as corrupted, by the various tissues (e.g., cerebro-spinal fluid, meninges, bone, galea, and scalp) interposed between the cortex and the recording electrodes. In short, EEG recordings have a low signal-to-noise (S/N) ratio.

The limitations associated with EEG data collection are partially addressed by recording cortical signals directly from the brain surface (electrocorticography or ECoG) or from certain subcortical structures such as the amygdalae or hippocampi (depth electroneuronography). The limited human resources (e.g., neurosurgeons), the need for sophisticated, expensive equipment, and the risks inherent in breaching the dura and accessing the brain make this alternative impractical or unavailable to many patients, and greatly limit accessibility to pharmaco-resistant epilepsy patients (approximately 900,000 in the US and 20 million globally) who would be candidates for therapies requiring cranio-cerebral surgery.

Therefore, it would be desirable to have systems for reliably acquiring and monitoring high quality electrical brain activity, particularly from deep structures without resorting to craniotomy or even burr holes for placement of electrodes, sensors, or therapy means. Moreover, recording of signals directly from cortex overlaying the skull base (e.g., orbito-frontal, basal temporal) using state-of-the-art approaches is technically more cumbersome and more traumatic than from the hemispheres' convexities. Thus, it is desirable and valuable to develop systems, methods, procedures, and/or devices that readily allow acquisition of brain signals (e.g., electrical, chemical, mechanical, thermal) and/or delivery of therapies, especially regarding deep brain structures, while having the advantages of being less technically demanding to implant (allowing implantation by ear, nose, and throat specialists and interventional radiologists in addition to neurosurgeons; facilitating outpatient surgery without compulsory hospitalization; avoidance of general anesthesia in favor of conscious sedation and/or local anesthesia). Achieving these aims would cost-effectively further epilepsy care.

SUMMARY OF THE INVENTION

In one embodiment, the present disclosure relates to an implantable sensor system for sensing biological signal of a patient comprising: an anchor for coupling the sensor to at least one patient skull base structure; a first sensor coupled to the anchor for sensing, at a first location proximate to the at least one patient skull base structure, at least one biological signal of a patient; and a transmitter coupled to the sensor and capable of transmitting data from the sensor to an external device.

In one embodiment, the present disclosure relates to an implantable sensor system for sensing biological signal of a patient comprising: an anchor for coupling the sensor to at least one patient skull base structure; a first sensor coupled to the anchor for sensing, at a first location proximate to the at least one patient skull base structure, at least one biological signal of a patient; a transmitter coupled to the sensor and capable of transmitting data from the sensor to an external device; and a conductor connecting the transmitter and the sensor.

In one embodiment, the present disclosure relates to an integrated implantable sensor system for sensing biological signal of a patient comprising: an anchor for coupling the sensor to at least one patient skull base structure; a first sensor coupled to the anchor for sensing, at a first location proximate to the at least one patient skull base structure, at least one biological signal of a patient; a transmitter coupled to the sensor and capable of transmitting data from the sensor to an external device; and a housing to which each of the anchor, the sensor, and the transmitter are coupled.

BRIEF DESCRIPTION OF THE DRAWINGS

The disclosure may be understood by reference to the following description taken in conjunction with the accompanying drawings, in which like reference numerals identify like elements, and in which:

FIG. 17B shows exemplary sensor placements in proximity to the foramen *lacerum* (lateral view of skull), in accordance with embodiments of the present disclosure.

DESCRIPTION OF ILLUSTRATIVE EMBODIMENTS

In one aspect, the present disclosure provides an implantable sensor system for sensing biological signals of a patient, such as brain activity of the patient. Embodiments of the present disclosure provide for a skull base or facial bones implantable system that includes a sensor positioned proximate the base of the skull or facial bones of a patient. A facial bone or a portion of the skull base may be termed a "patient skull base structure". The skull base/facial bones implantable system may be coupled to another implanted device positioned elsewhere in a patient's body or to an external device that communicates with an implanted sensor via wireless communications.

Figure 1A:
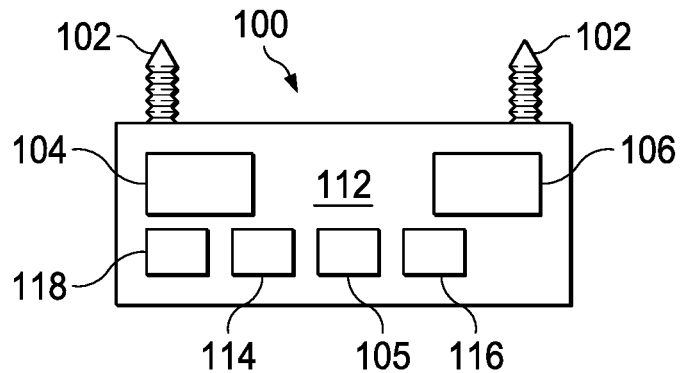
FIG. 1A depicts an implantable sensor system for implantation in a head of a patient, in accordance with one embodiment of the present disclosure.
Figure 1B:
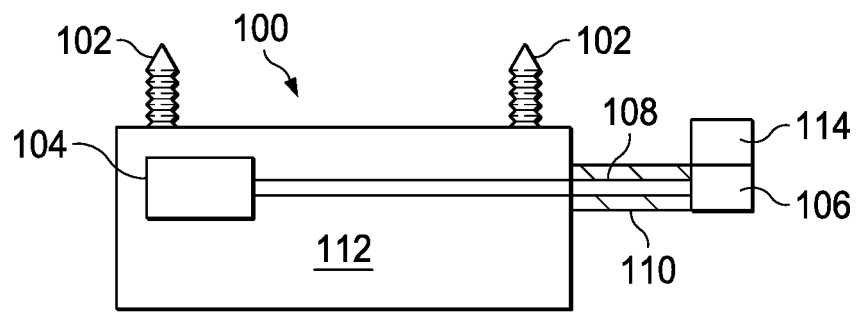
FIG. 1B depicts an implantable sensor system for implantation in a head of a patient, in accordance with one embodiment of the present disclosure.

In FIGS. 1A and 1i, an implantable sensor system 100 comprises one or more anchor(s) 102. Each of the anchor(s) 102 is configured for coupling the sensor 100 to at least one structure in or proximate to the base of the skull and/or facial bones of the patient. The anchor 102 may comprise at least one of a bone screw, a helical screw, a plate, a flange, a pin, a hook, a barb, a tine, a prong, a rivet, a spring, an adhesive, a cement, a glue, a bone plug, a compressible element, or a grooved connection. For example, FIGS. 1A and 1B show anchors 102 comprising a bone screw, although many suitable anchor types may be used.

In one embodiment, the anchor(s) 102 and/or other elements of the implantable sensor system 100 may comprise an osteoconductive material. The use of an osteoconductive material, such as titanium, in at least part of the device, may stimulate incorporation of the device into the bone. An osteoconductive material may be particularly desirable when the anchor 102 comprises an adhesive, a cement, or a glue.

The implantable sensor system 100 may also comprise a sensor 104 coupled to the anchor(s) 102. Sensor 104 may be configured for sensing, at a first location proximate to at least one patient skull base or facial bone structure, at least one biological signal of the patient. The sensor 104 may be at least one of an electrode, a pressure sensor, a thermal sensor, a photonic sensor, or a chemical sensor, among others. In some embodiments, the sensor 104 may sense body data from at least one of a brain, a cranial nerve, and a cranial blood vessel at a first patient skull base or facial bone location proximate to neural or vascular structures of interest.

The implantable sensor system 100 may also comprise a transmitter 106, which may be coupled to the sensor 104. The transmitter 106 may be capable of transmitting data from the sensor 104 to an external device (e.g., FIG. 7, element 700, discussed in more detail hereafter).

The implantable sensor system 100 may further comprise a second sensor 105 coupled to the anchor 102 for sensing, at a second location proximate to the at least one patient skull base structure, at least a second biological signal of said patient. The second sensor 105 may be at least one of an electrode, a pressure sensor, a thermal sensor, a photonic sensor, or a chemical sensor, among others.

The transmitter 106 and the sensor 104 may be located in a housing 112, as shown in FIG. 1A, or the transmitter 106 may be located outside of housing 112 at a distance from the sensor 104 (FIG. 1), such as underneath or on a skin surface of the patient. Transmitter 106 may, but need not, be lateral to (further from the patient's midline than) the housing 112 discussed below. (Alternatively, the housing 112 may be considered to be medial to (closer to the patient's midline than) the transmitter 106).

In one embodiment, transmitter 106 may be adapted for epidermal placement, such as by use of an adhesive patch, a bandage, or the like. In other embodiments, transmitter 106 may be housed in an article worn by the patient (e.g., a pair of eyeglasses, an earring, a housing adapted for over-the-ear placement, or the like).

In the embodiment depicted in FIG. 1B, a conductor 108 (e.g., a wire) may connect the transmitter 106 and the sensor 104. The conductor 108 in this embodiment may pass through subcutaneous tissues of the patient's head or face. Conductor 108 may be wire housed in and insulated by a conduit 110.

Returning to FIG. 1A, the implantable sensor system 100 is shown as an integrated device comprising a housing 112, to which the anchor(s) 102, the sensor 104, and the transmitter 106 are coupled. The anchor(s) 102 may be connected but generally external to the housing 112 and various elements (e.g., sensor 104, transmitter 106) may be enclosed within the housing 112. In one embodiment, the anchor(s) 102 and the sensor 104 may be considered one and the same.

Alternative arrangements of the various elements shown in FIGS. 1A-1B relative to the housing 112 are possible.

The implantable sensor system 100 may further comprise one or more additional elements. For example, the implantable sensor system 100 may further comprise a power supply 114, which may provide power for at least one of the transmitter 106 or the sensor 104 (if the sensor 104 is an active device requiring power). As shown in FIG. 1A, the power supply 114 may be located proximate to the sensor 104 (and/or the transmitter 106), such as at a location within or coupled to the exterior of the housing 112. FIG. 1B depicts the power supply 114 located at a distance from the sensor 104 and housing 112, proximate to transmitter 106 near an external surface of the patient's skin. The conductor 108 may be configured to deliver power from the power supply 114 to the sensor 104 (if the sensor 104 is an active sensor), or another power delivery structure (e.g., housed within the conduit 110) may be used. In one embodiment, the power supply 114 may be rechargeable.

Implantable sensor system 100 may further comprise circuitry 116 for processing a biological signal of the patient received from the sensor 104, prior to the transmission of the signal by the transmitter 106. The circuitry 116 may comprise any appropriate signal-conditioning and/or processing circuits, with multiple circuits present as any combination of discrete circuits and/or components of an integrated circuit. In a particular embodiment, the circuitry 116 comprises an integrated circuit having one or more of a filter, an amplifier, a D/A converter, an A/D converter, or any other circuit configurable to condition, amplify, or otherwise process biological signals in "noisy" environments.

Figure 7:
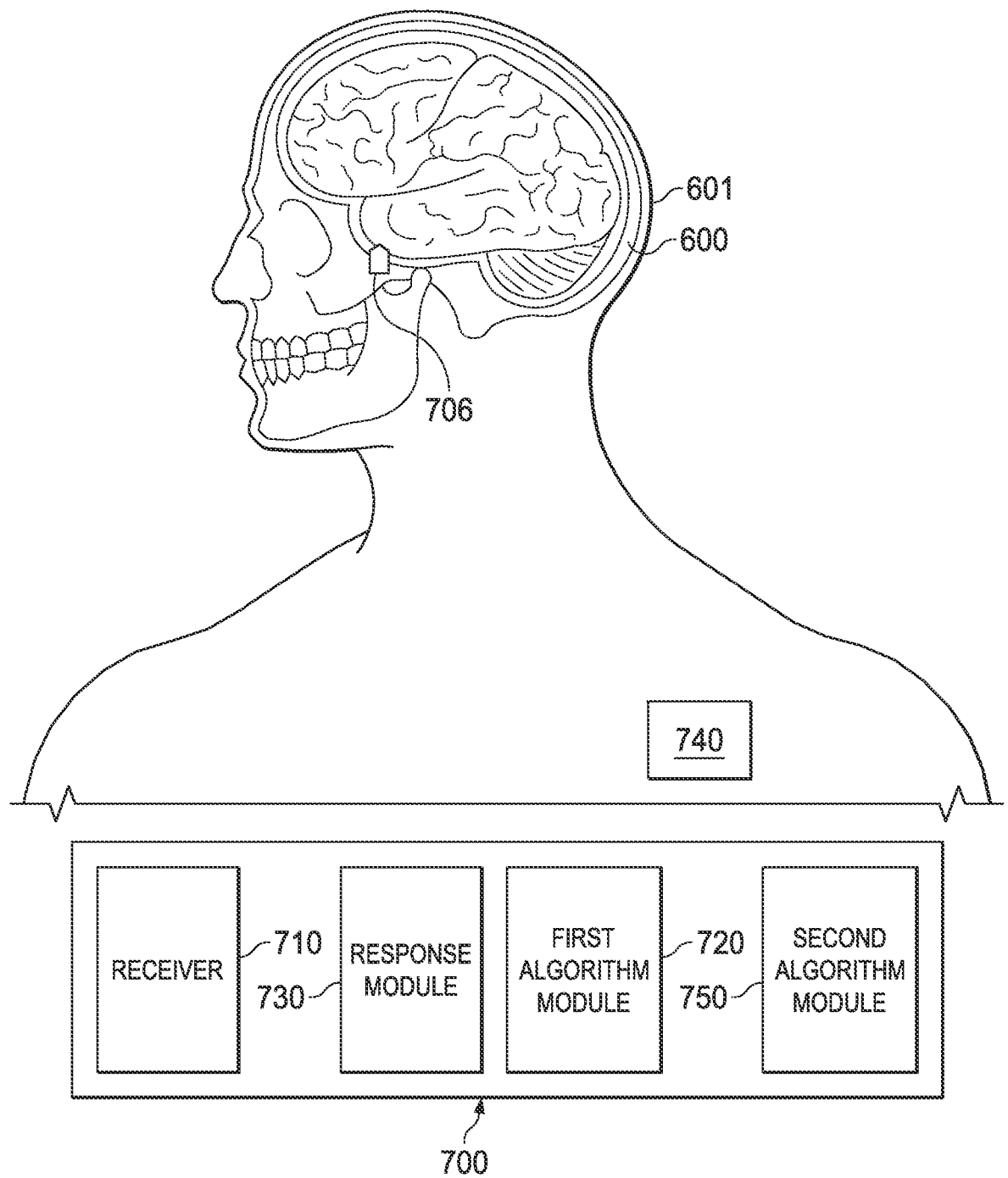
FIG. 7 depicts an external device, in accordance with one embodiment of the present disclosure.

Implantable sensor system 100 may further comprise a receiver 118 coupled to the sensor 104 and capable of receiving data from an external device 700 (FIG. 7). The received data may include data suitable for initiating, modifying, or terminating sensing by the sensor 104. The controller of the receiver 118 may be located in the housing 112 or the external device 700.

Alternatively or in addition to the transmitter 106, one or more other components of the implantable sensor system 100 may be adapted for subcutaneous, epidermal, or external placement. In one embodiment, for example, only the anchor(s) 102, sensor 104, and housing 112 may be implanted in the body of the patient proximate the skull base or facial bones, and the other components discussed with reference to FIG. 1A or 1B may be located external to the patient's body (e.g., in one or more of an external patch, an external computing device such as a smartphone, a tablet computer, a notebook computer, or another externally located device).

Figure 2:
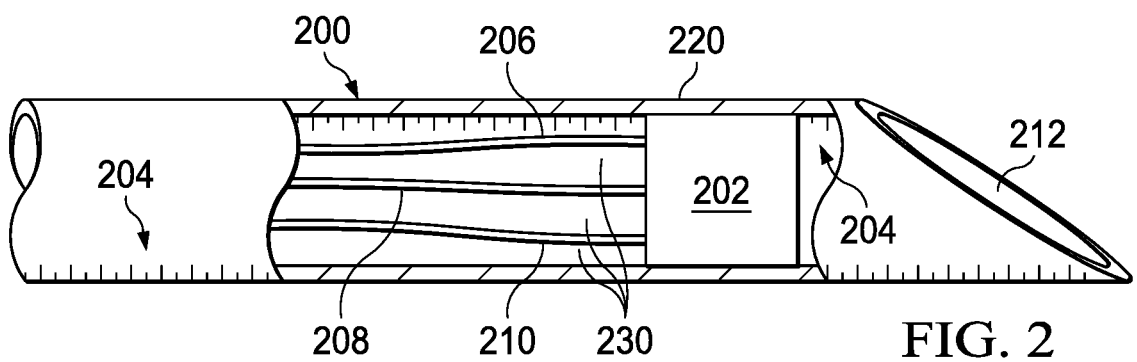
FIG. 2 depicts components of a kit for implanting a biological signal sensor in a head of a patient, in accordance with one embodiment of the present disclosure.

The present disclosure also relates to a kit for implanting a biological signal sensor in a head of a patient. The kit may comprise a sealed container having sterilized components suitable for implanting the biological signal sensor. In various embodiments, the sterilized components may comprise those depicted in one or more of FIGS. 2-7. In one embodiment, one or more components of an implantable sensor (e.g., as depicted in FIG. 1A or 1B) may be delivered to a target site proximate a skull base structure via a cannula (as shown in FIG. 2) traveling beneath the patient's skull table. When the cannula tip is located immediately beneath the skull table target site, the sensor may be expelled from the cannula tip and anchored to the skull base structure using, e.g., anchors 102 as shown in FIGS. 1A and 1B.

FIG. 2 depicts an embodiment of one such component, a cannula assembly 200. The cannula assembly 200 may comprise an outer wall 220 and a hollow bore 230. The cannula assembly 200 may be configured for introducing an implantable sensor 202 through the face of a patient and delivering the sensor to a desired target near a skull base structure or facial bone of the patient. The implantable sensor 202 may be placed inside the hollow bore 230 of the cannula assembly 200, and its position may be adjusted within the hollow bore 230 by use of actuators 206, 208, and/or 210. In particular examples, the actuators 206, 208, and/or 210 may comprise at least one of a plunger mechanism, a spring element, an obturator, or another movable member within hollow bore 230 of the cannula assembly 200. To aid in implanting the implantable sensor 202 at the target location, the cannula assembly 200 may comprise a ruler or other distance gauge 204. For example, the ruler 204 may comprise a millimetric scale to measure the distance between a piercing tip 212 of the cannula assembly 200 and a fiducial point such as the patient's facial epidermis or the zygoma. The ruler 204 may be considered a "cannula positioning element." Alternatively or in addition, other components of a kit, such as a mandrel, tray, or secondary mandrel, as will be shown in FIGS. 3-5, may comprise a ruler, scale, or other distance gauge to facilitate positioning of that component or those components during the process of implanting the sensor 202.

The implantable sensor 202 may comprise one or more elements of the implantable sensor system 100 described supra. In one embodiment, the implantable sensor 202 may comprise an anchor such as anchor 102 (FIGS. 1A, 1B) for coupling the sensor to at least one patient skull base or facial bone structure; a sensor coupled to the anchor for sensing, at a first location proximate to the base of the patient's skull or a facial bone, at least one biological signal of the patient, such as a brain activity (e.g., a thermal, a chemical, and/or an electrical brain activity), a vascular activity (e.g., blood pressure, pulse rate, temperature), a respiratory activity (e.g., oxygen saturation, respiratory rate), or a kinetic activity (e.g., amplitude, direction, and/or velocity of movement, such as may be measured with an accelerometer) of the patient; and a transmitter coupled to the sensor and capable of transmitting data from the sensor to an external device.

Figure 3A:
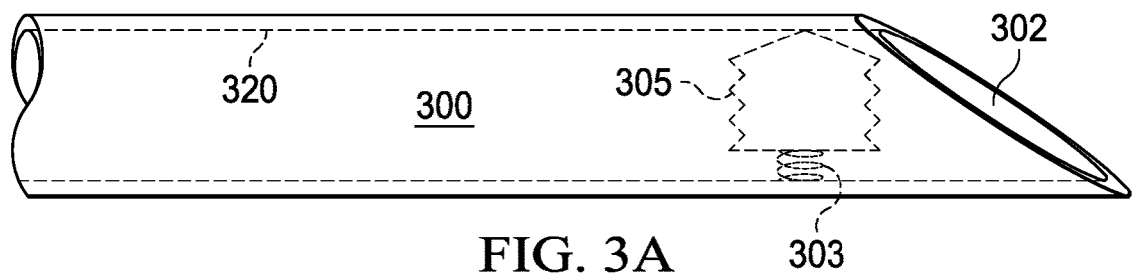
FIG. 3A depicts components of a kit for implanting a biological signal sensor in a head of a patient, in accordance with one embodiment of the present disclosure.

Turning to FIG. 3A, the cannula assembly 300 may comprise a piercing element 302. The piercing element 302 may comprise any sharp surface(s) adapted to dissect and penetrate tissues of the patient's head. Also depicted in FIG. 3A is an implantable sensor system 305 disposed within the cannula assembly 300 and a spring 303 for displacing the implantable sensor system 305 to a desired location proximate the skull base or other structure. Specifically, the implantable sensor system 305 and the spring 303 may be advanced in the cannula assembly 300 by any appropriate (reversible or irreversible) actuator (such as 206, 208, and/or 210, FIG. 2). Upon advancement of the implantable sensor system 305 to a position where its upper portion is no longer in contact with the wall 320 of the cannula assembly 300, the spring 303 will release, propelling the implantable sensor system 305 in an upward direction, to a location where its implantation is desired.

In other embodiments (not shown), a pneumatic or hydraulic propulsion device may be used instead of or in addition to the spring 303 in the placement of the sensor at the location where its implantation is desired.

Figure 3B:
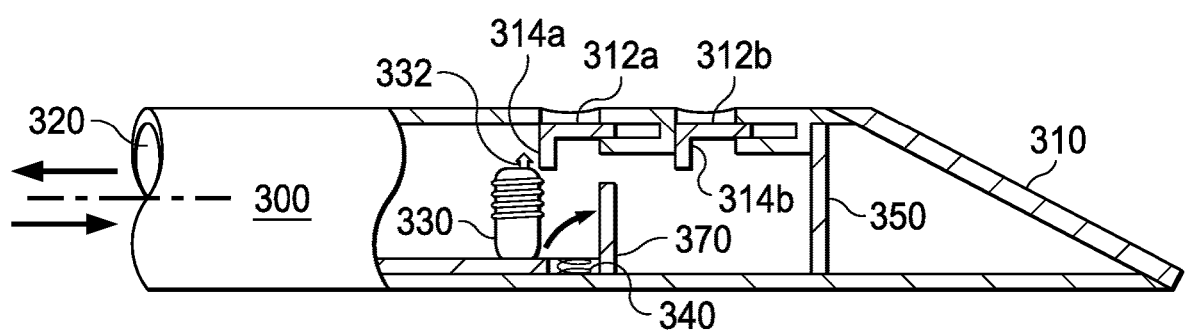
FIG. 3B depicts components of a kit for implanting a biological signal sensor in a head of a patient, in accordance with one embodiment of the present disclosure.

In another embodiment, as depicted in FIG. 3B, a cannula 300 may comprise a closed distal portion 310 and slidable gates 312a, 312b, each of which may comprise an elastic gate knob, such as elastic gate knobs 314a, 314b. In other embodiments (not shown), the cannula 300 may comprise one slidable gate 312a, three slidable gates 312a-c, or other numbers of slidable gates 312. Sliding of the slidable gates 312*a*, 312*b* may be effected by elastic gate knobs 314*a*, 314*b*.

The sensor 330 (shown here on a slidable tray (not numbered)), slidable gates 312, and elastic gate knobs 314, may be configured such that, upon displacement of the sensor 330 and/or the tray in a distal direction (toward 310), the sensor 330 itself, an anchor, such as barb 332, or other structure disposed on the sensor 330 may engage elastic gate knob 314 and advance the slidable gate 312 into a recess formed in the wall of the cannula 300 (i.e., the slidable gate 312 is moved from a closed conformation to an opened conformation). Upon further advancement of the sensor 330, the slidable gate 312 becomes maximally advanced. Upon continuing advancement of the sensor 330, the elastic gate knob 314 slides over the barb 332 and retracts to its original position. In certain embodiments, the slidable gate 312 may return to a closed conformation when the tray carrying sensor 330 is pulled backwards (towards the proximal opening of the cannula).

The sensor 330 and/or the tray may be displaced within the bore of the cannula 300 by a slidable mandrel (not shown); gears and chains may also slide the tray carrying sensor 330 and/or sensor 330 itself. In other words, the sensor 330 may be moved independently of the tray. In other embodiments, two or more sensors 330 may be displaced within the bore of the cannula. The sensor 330 may be locked into a position relative to the slidable mandrel by a pivoting gate 370. The pivoting gate 370 may be pivoted (such as by release of a latch, not shown) to allow positioning of the sensor 330 in a pre-displacement position above a loaded spring 340. The distal displacement of the slidable mandrel may be limited by a stopgage 350. Upon positioning of the sensor 330 at an appropriate point within the bore of the cannula 300, a slidable gate 312 may be opened (or may have already been open) and the sensor 330 propelled by action of the spring 340 out the slidable gate 312 to a location where its implantation is desired. The spring's tensile force may vary according to the size, shape, and anchoring mechanism of the sensor 330 as well as the physical and geometrical properties of the bone housing the sensor.

In other embodiments (not shown), a pneumatic or hydraulic propulsion device may be used to deploy the sensor 330 instead of or in addition to the loaded spring 340 (which may allow simplification of the cannula design). In still other embodiments, other techniques for deploying the sensor, e.g., a push rod, a mandrel, a gear, a rotatable element, etc. may be used.

Figure 4A:
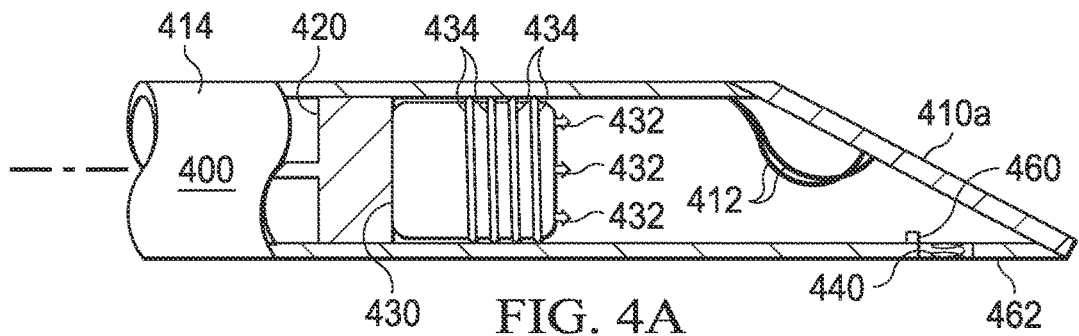
FIG. 4A depicts components of a kit for implanting a biological signal sensor in a head of a patient, in accordance with one embodiment of the present disclosure.

Turning to FIG. 4A, one embodiment of a cannula assembly 400 configured for implantation of a sensor 430 is presented. The sensor 430 is configured such that its housing is substantially cylindrical; the shape of the cannula may vary depending on the clinical application and site of implantation of the sensor. The housing of the sensor 430 may comprise one or more anchors, such as barbs 432 and/or threads 434. Although both barbs 432 and threads 434 are shown in FIG. 4, in various embodiments, only one or the other anchor type may be present. In other words, the body of the sensor 430 may form its own anchoring structure. The sensor 430 may be positioned coaxially within the bore of the cannula assembly 400.

The cannula assembly 400 may comprise a pivotable stopgage 410 in original position 410*a*, which is restrained by one or more elastic tethers 412, and a loaded spring 440, held in its loaded position by a latch 460 controlled by a latch housing 462. The cannula assembly 400 may also comprise a slidable mandrel 420 configured to advance the sensor 430 in the cannula.

Alternatively, the cannula assembly 400 may comprise one or more other sensor repositioning elements (not shown), such as one or more of ramps, stops, spring elements, pivoting elements, rotational elements, gears, mandrels, etc.

Figure 4B:
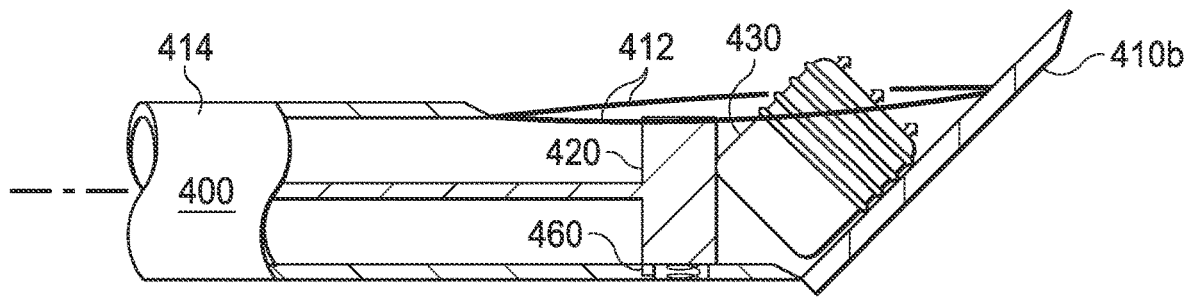
FIG. 4B depicts components of a kit for implanting a biological signal sensor in a head of a patient, in accordance with one embodiment of the present disclosure.

FIG. 4B shows a second position of the sensor 430 relative to cannula assembly 400. The slidable mandrel 420 has advanced the sensor 430 such that the stopgage 410 has been deployed into a position 410*b* and elastic tethers 412 are held in an extended position by force applied by slidable mandrel 420 through sensor 430 to stopgage 410. Although latch 460 has been opened, slidable mandrel 420 may be sized and shaped such that it prevents release of loaded spring 440 until retracted.

Figure 4C:
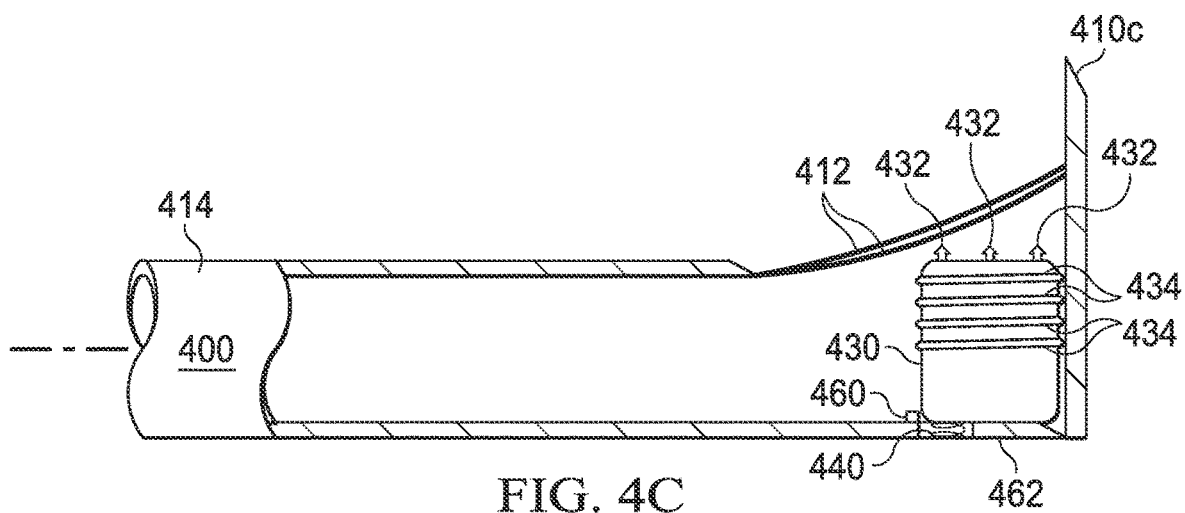
FIG. 4C depicts components of a kit for implanting a biological signal sensor in a head of a patient, in accordance with one embodiment of the present disclosure.

FIG. 4C shows a third position of the sensor 430 relative to cannula assembly 400, in the instant before propulsion of the sensor 430 by spring 440. Upon retraction of the slidable mandrel 420, the force holding elastic tethers 412 in the extended position of FIG. 4B is removed, and elastic tethers 412 may return to a relaxed conformation and/or their point of attachment in the ceiling of the cannula assembly 400 may slide in a proximal direction. The stopgage 410 is deployed into a position 410*c*, with further return toward 410*a* prevented by the sensor 430, and relapse toward 410*b* prevented by elastic tethers 412 as no further force is being applied by the mandrel 420. The alternating forces of the mandrel in one direction and of the tethers 412 and the stopgage 410 in the opposite direction may cause the sensor to change its alignment (in reference to the cannula's longest axis) from co-axial to orthogonal.

In the particular depicted example, upon positioning the cannula assembly 400 near a suitable location for implantation, and positioning of the sensor 430 as shown in FIG. 4C, the sensor 430 may be deployed from the cannula assembly 400, such as by releasing the spring 440 by causing the latch housing 462 to release the latch 460. The sensor 430 may then be propelled to the target location.

Figure 4D:
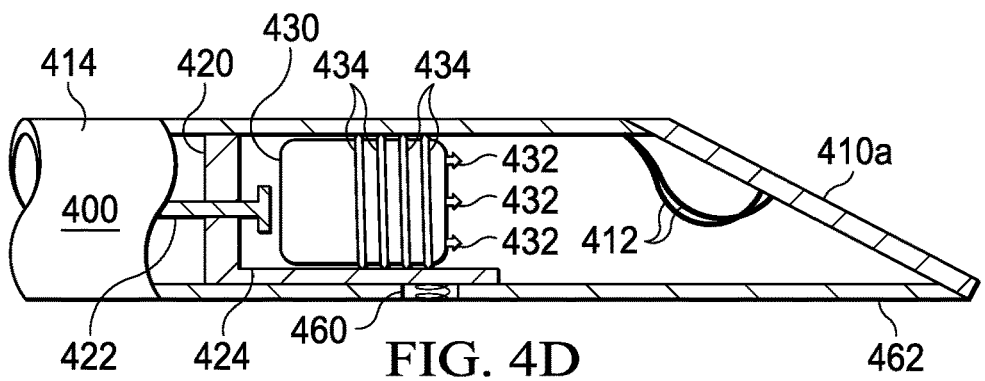
FIG. 4D depicts components of a kit for implanting a biological signal sensor in a head of a patient, in accordance with one embodiment of the present disclosure.

FIG. 4D depicts an alternative embodiment of the relationship between mandrel 420 and sensor 430. In this embodiment, the mandrel 420 may comprise a ledge 424 on which the sensor 430 may be placed. The mandrel 420 may also comprise a secondary mandrel 422 which is slidable relative to the mandrel 420. The secondary mandrel 422 may have its own positioning and adjusting structures (not shown). When the mandrel 420 is retracted from its position in FIG. 4B, a secondary mandrel 422 may be moved in the distal direction, or may be held in a fixed position relative to the cannula assembly 400 (not shown). In the first case, the secondary mandrel 422 moves relative to mandrel 420. The movement of the mandrel 420, secondary mandrel 422, or of both (420 & 422) may push the sensor 430 off the ledge 424 of mandrel 420, such as at a position of mandrel 420 when the sensor 430 is disposed above spring 460. Given its direct contact with spring 460, the movement of the mandrel 420 in the proximal direction may release spring 460 such that spring 460 may propel sensor 430 in a direction orthogonal to the longitudinal axis of the cannula assembly 400, and to the target location of sensor 430.

Figure 5A:
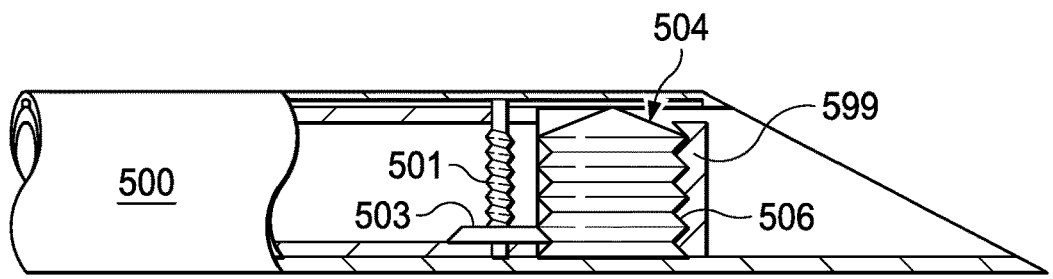
FIG. 5A depicts components of a kit for implanting a biological signal sensor in a head of a patient, in accordance with one embodiment of the present disclosure.
Figure 5B:
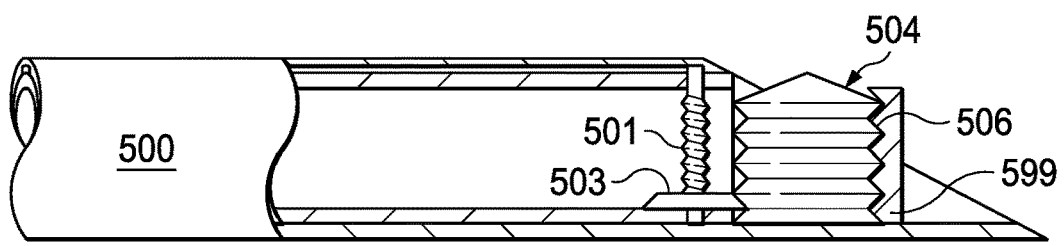
FIG. 5B depicts components of a kit for implanting a biological signal sensor in a head of a patient, in accordance with one embodiment of the present disclosure.
Figure 5C:
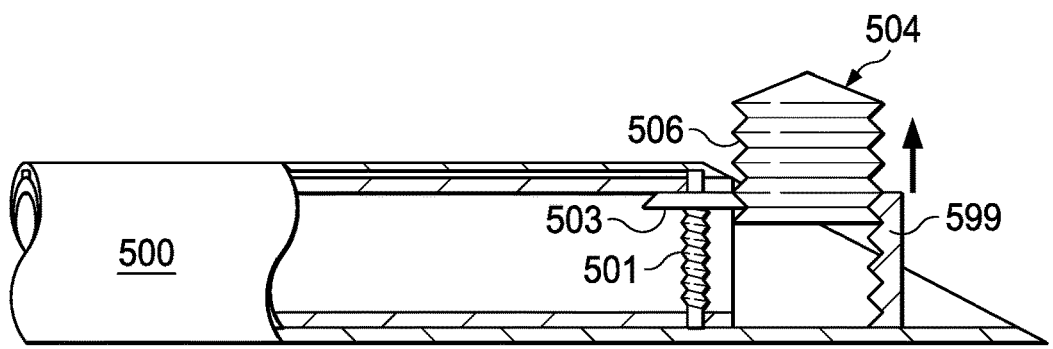
FIG. 5C depicts components of a kit for implanting a biological signal sensor in a head of a patient, in accordance with one embodiment of the present disclosure.

FIGS. 5A-5C depict an embodiment wherein a sensor 504 is initially positioned in an axially perpendicular arrangement within the bore, rather than a coaxial arrangement. Although this arrangement is less compact than a coaxial arrangement as depicted in FIG. 4A, such an arrangement may provide easier deployment from cannula 500.

In FIG. 5A, the implantable sensor 504 is depicted as being deployed subsequent to helical engagement of threads 506 with sensor advancement gear 503 on movable threaded rod 501. In one embodiment, the movable threaded rod 501 does not rotate on its own axis (e.g., it is rotationally fixed). The movable threaded rod 501 and/or gear 503 may be rotated by gears or chains (not shown) operable from the proximal end of the cannula 500; a slidable mandrel/tool engineered to rotate gear 503 endowed with cogs, may be also used as well as other structures discussed elsewhere herein (not shown in FIGS. 5A-5C).

FIG. 5B shows in more detail an intermediate deployment. The movable threaded rod 501 and gear 503 have been moved forward, such as by engagement of the rod 501 with a slidable mandrel or other structure (not shown), such that the sensor advancement gear 503 has remained in its initial orientation with respect to the cannula assembly 500 and the sensor 504. A support structure 599 may secure the sensor 504 during operation of the sensor advancement gear 503.

FIG. 5C shows a final step in deployment of the sensor 504. The movable threaded rod 501 or the gear 503 has been rotated, such that the sensor advancement gear 503 has threadably engaged threads 506 of the sensor 504, thereby rotating and advancing the sensor 504 toward a position proximate the skull base at which sensing is desired.

FIGS. 3A-5C depict illustrative embodiments of deploying sensors. The person of ordinary skill in the art, having the benefit of the present disclosure, will be aware of alternative techniques for the deployment of sensors of the present disclosure.

Though not shown in the figures, a cannula, e.g. 200, 300, 400, or 500 may further comprise a scout sensor. The scout sensor may be configured for sensing at least one of the position of the cannula or the proximity of the cannula to at least one anatomical structure. The scout sensor may comprise at least one of an electrical, thermal, pressure or optical/video sensor to detect tissue that may be desirable for monitoring or that should be avoided by the cannulae so as to not damage it. For example, it would be undesirable to damage cranial nerves or rupture blood vessels as the cannula is advanced towards its intended target. For a particular example, damage to the trigeminal nerve is a complication of placement of a sensor as described herein near a foramen *ovale* of a patient. Without a positioning device such as the scout sensor, the cannula may inadvertently pierce parts of the brain, such as the brainstem, causing neurological deficits, infections, or other adverse consequences. These risks may be minimized by incorporating a scout sensor into the cannula to indicate its proximity to sensitive or critical tissues or structures.

Although a number of techniques and structures for implantation of a sensor have been presented, the person of ordinary skill in the art having the benefit of the present disclosure may deploy a sensor using apparatus and techniques other than those disclose herein as a matter of routine skill. For example, an implantable sensor system may be placed in a desired location in or near the skull base or facial bones by endoscopy.

Figure 6:
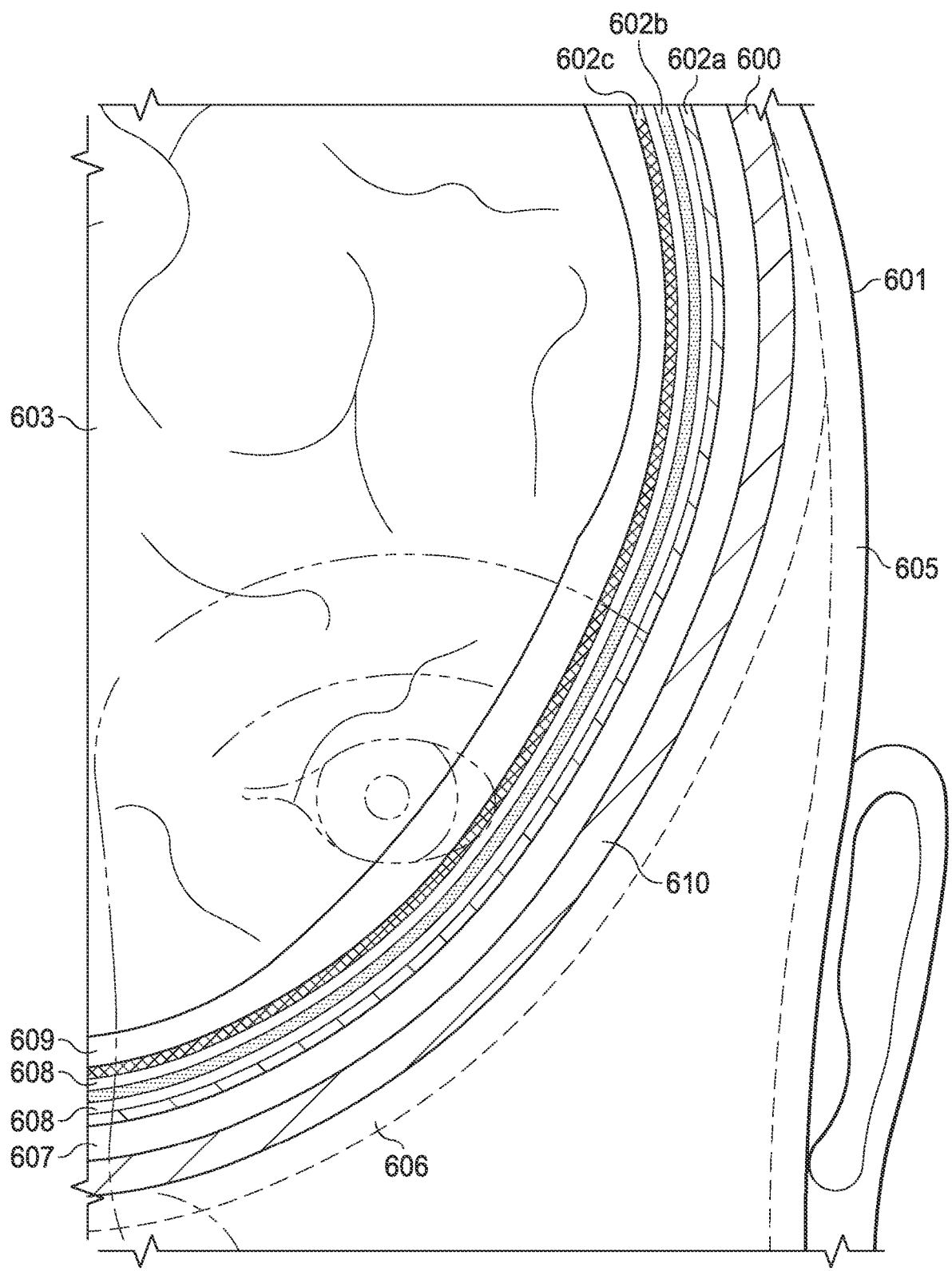
FIG. 6 schematically represents various anatomical structures of the human head (coronal view), and various sites defined with reference to one or more of those anatomical structures, in accordance with one embodiment of the present disclosure.

FIG. 6 is a coronal view (not to scale) of a lower quadrant of a patient's head, depicting various structures of the human head to which one or more components of the implantable sensor system 100 may be coupled. The base of the skull 600 and the scalp and/or skin 601 have been mentioned above. Inward from the base of the skull are three meningeal membranes, the dura mater 602a (closest to the calvarium, the inner surface of the skull 600), the arachnoid mater 602b, and the pia mater 602c, which is apposed to the cortex. Most inward in this figure is the patient's brain 603.

For the sake of clarity the following terms will be defined: The epidermis 601 is the layer of skin in direct contact with the environment. The outer surface/table of the skull 600 is the epicranium, which is covered by the galea 606, which in turn is beneath the scalp 605; the space between the outer and inner surfaces of the skull 600 is the diploe 610, and its innermost surface is the calvarium. Intra-osseous refers to a location 610 between the outer and innermost skull tables.

In one embodiment, a first target location may be selected from a subcutaneous location 605, an epicranial location 606, an intra-osseous (i.e., within the skull) location 610, an epidural location 607, a subdural location 608, an epicortical location 609, or an intra-parenchymal location 603. A subcutaneous location 605 herein refers to a location in or within a layer of the skin 601 below the epidermis, and above or on an outer surface of underlying muscle, fat, or other soft tissue. An epicranial location 606 herein refers to a location in, among, or under muscle, fat, or other soft tissue of the head, and outside the skull 600. An epidural location 607 herein refers to a location inside the skull 600 and outside the dura mater 602a. A subdural location 608 herein refers to a location inside/beneath the dura mater 602a and outside the pia mater 602c. The subdural location 608 may be inside or outside the arachnoid mater 602b.

A number of sites on the skull base may be particularly useful as a target site for placement of one or more components of the implantable sensor system 100.

In one embodiment, the at least one target skull base structure may be selected from a bone structure of the skull base 600, a neural structure proximate the skull base 600, and a vascular structure proximate the skull base 600. Examples of such structures include, but are not limited to: bone; nerve trunk; blood vessel; ganglion; or brain.

Figure 10:
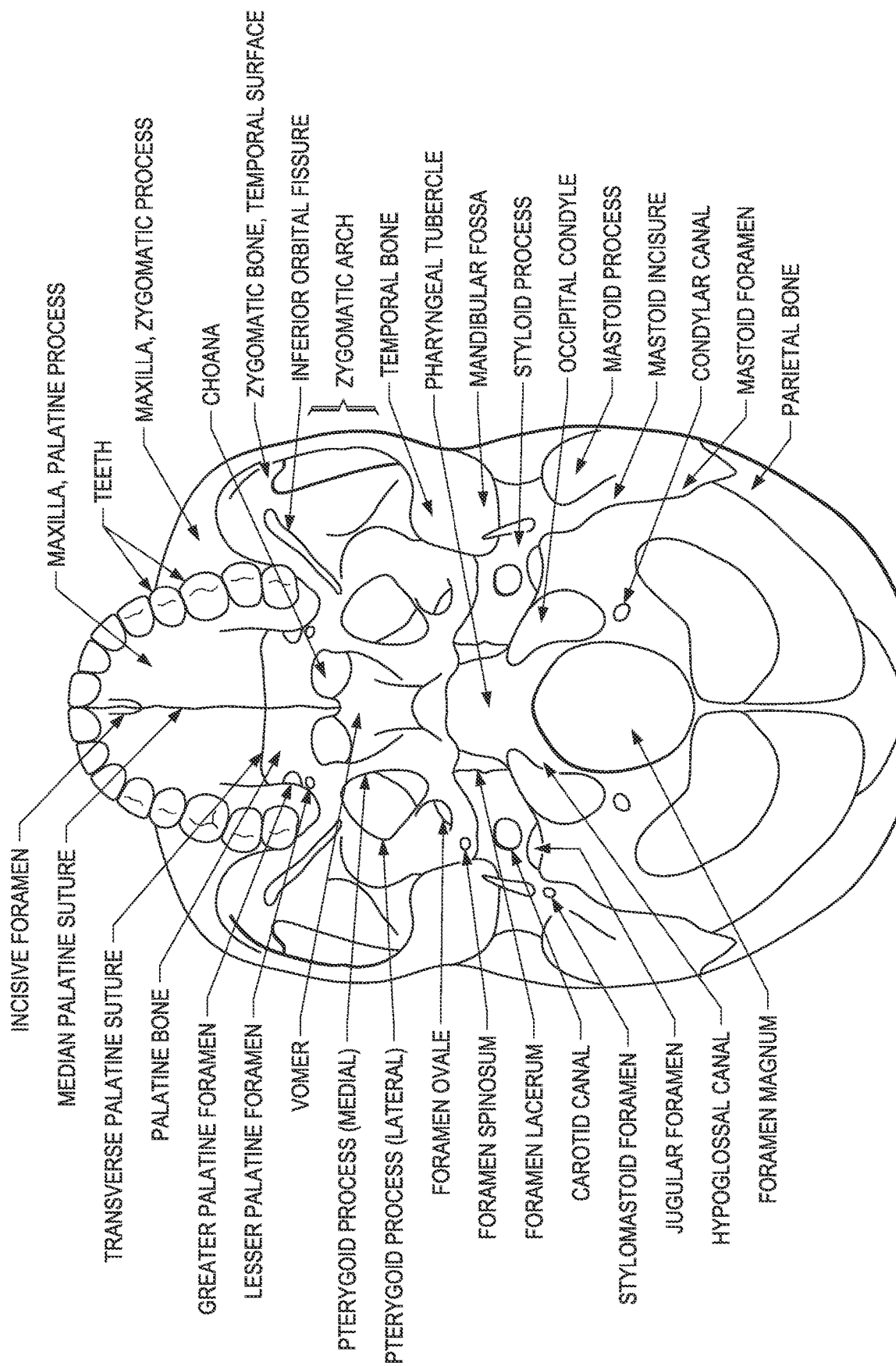
FIG. 10 shows a basal aspect of the human skull and various anatomical structures visible thereon.

FIG. 10 shows a basal aspect of the human skull and various anatomical structures in proximity to which a sensor according to embodiments of the disclosure may be coupled. These include the maxilla, palatine and zygomatic processes; the teeth; the choana; the temporal surface of the zygomatic bone; the inferior orbital fissure; the zygomatic arch; the temporal bone; the pharyngeal tubercle; the mandibular fossa; the styloid process; the occipital condyle; the mastoid process; the mastoid incisures; the condylar canal; the mastoid foramen; the parietal bone; the foramen magnum; the hypoglossal canal; the jugular foramen; the stylomastoid foramen; the carotid canal; the foramina *lacerum, spinosum*, and *ovale*; the pterygoid process, lateral and medial surfaces; the vomer; the greater and lesser palatine foramina; the palatine bone; the transverse and median palatine sutures; and the incisive foramen.

Figure 11:
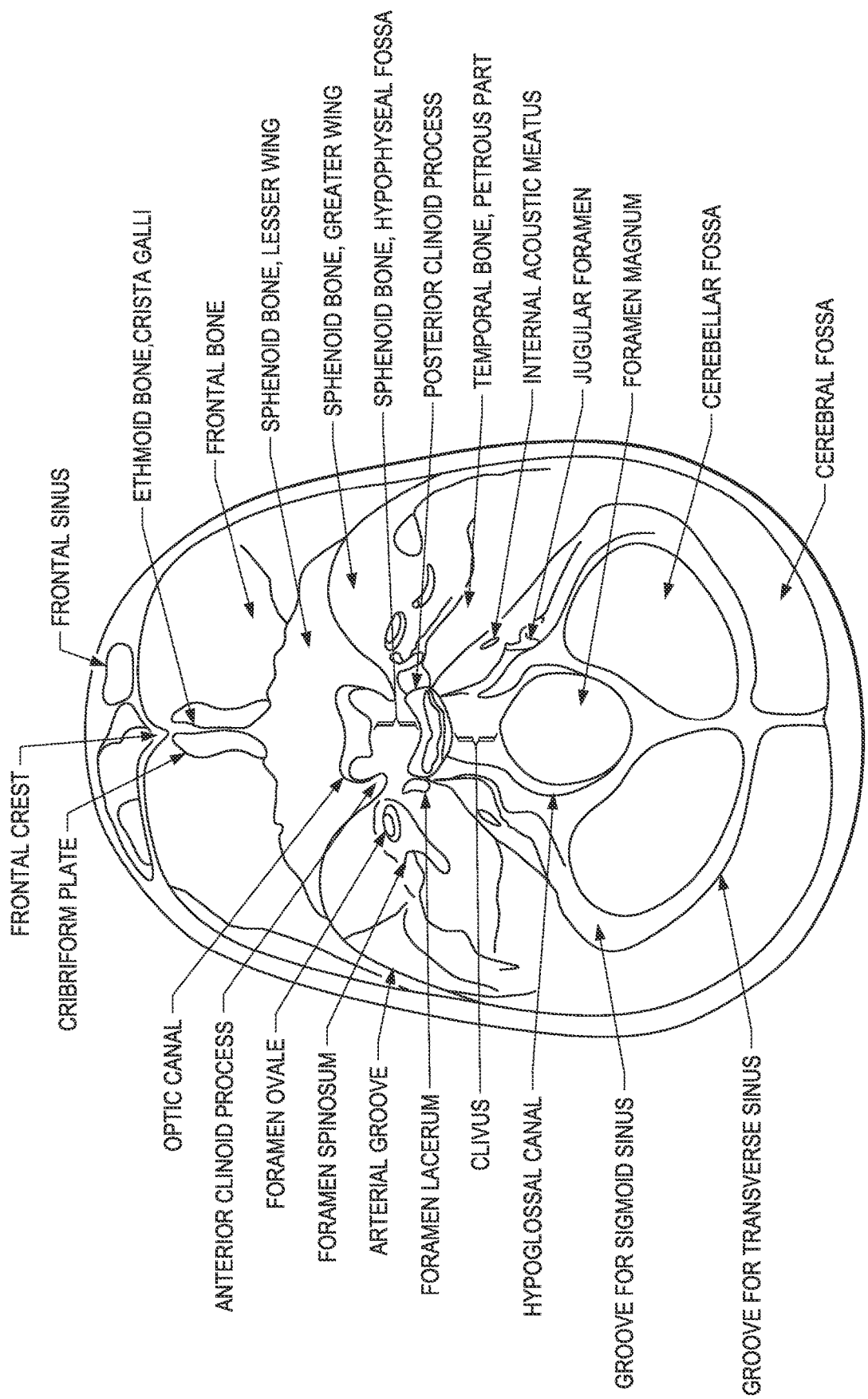
FIG. 11 shows an interior aspect of the human skull base and various anatomical structures visible thereon.

FIG. 11 shows an interior aspect of the human skull and various anatomical structures in proximity to which a sensor according to embodiments of the disclosure may be coupled. These include the frontal sinus; the ethmoid bone, *crista galli*; the frontal bone; the lesser wing, greater wing, and hypophyseal fossa of the sphenoid bone; the anterior and posterior clinoid processes; the petrous part of the temporal bone; the internal acoustic meatus; the jugular foramen; the foramen magnum; the cerebellar and cerebral fossae; the grooves for the transverse and sigmoid sinuses; the hypoglossal canal; the clivus; the foramina *lacerum, spinosum*, and *ovale*; the arterial groove; the optic canal; the cribriform plate; and the frontal crest.

Figure 12:
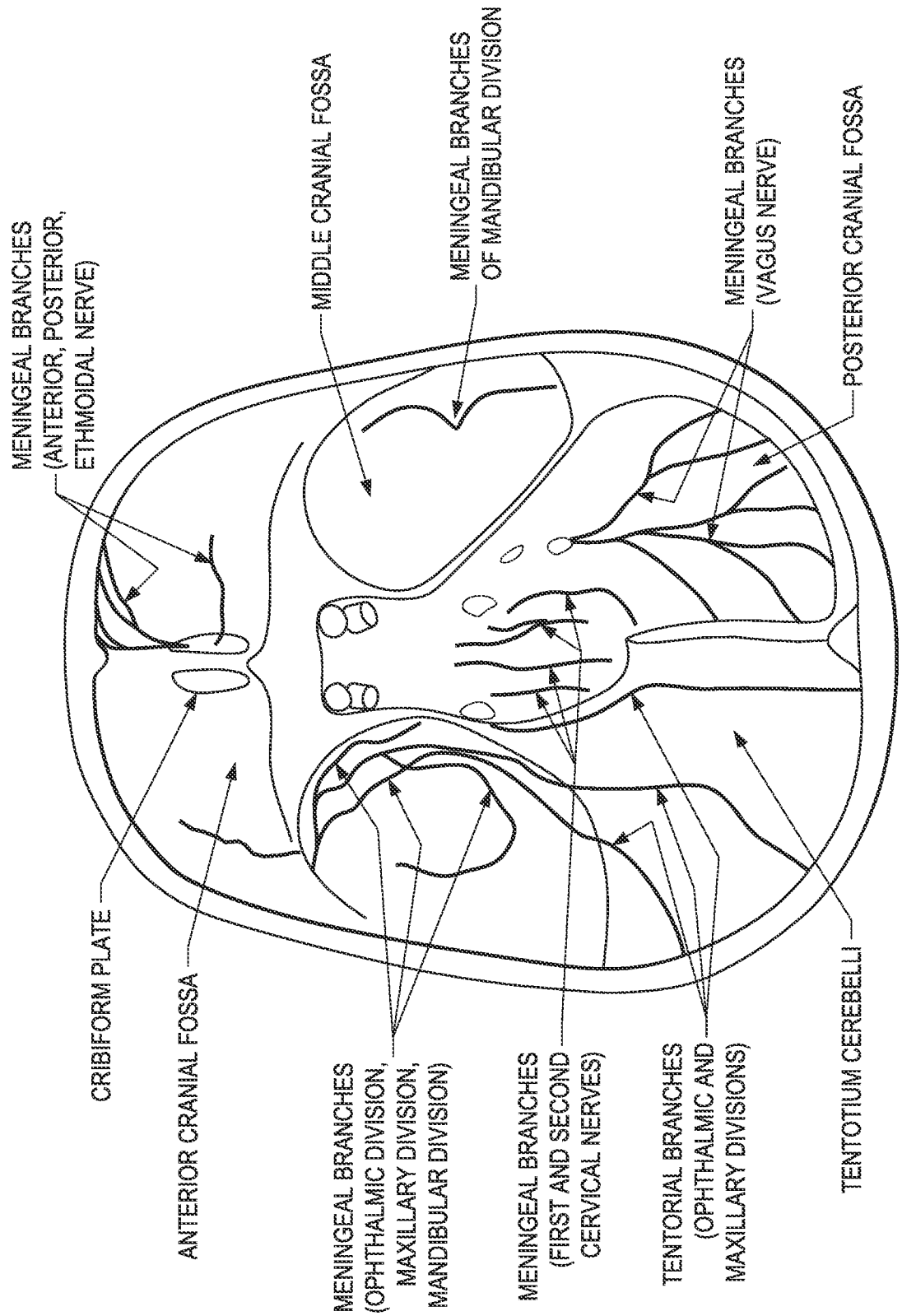
FIG. 12 shows the cranial fossae and nearby anatomical structures of the human skull base.

FIG. 12 shows the cranial fossae and nearby anatomical structures in proximity to which a sensor according to embodiments of the disclosure may be coupled. These include the anterior and posterior meningeal branches of the ethmoidal nerve; the anterior, middle, and posterior cranial fossae; the meningeal branches of the mandibular division; the meningeal branches of the vagus nerve; the tentotium cerebelli; the tentorial branches of the ophthalmic and maxillary divisions; the meningeal branches of the first and second cervical nerves; the meningeal branches of the ophthalmic and maxillary divisions; and the cribriform plate.

Figure 13:
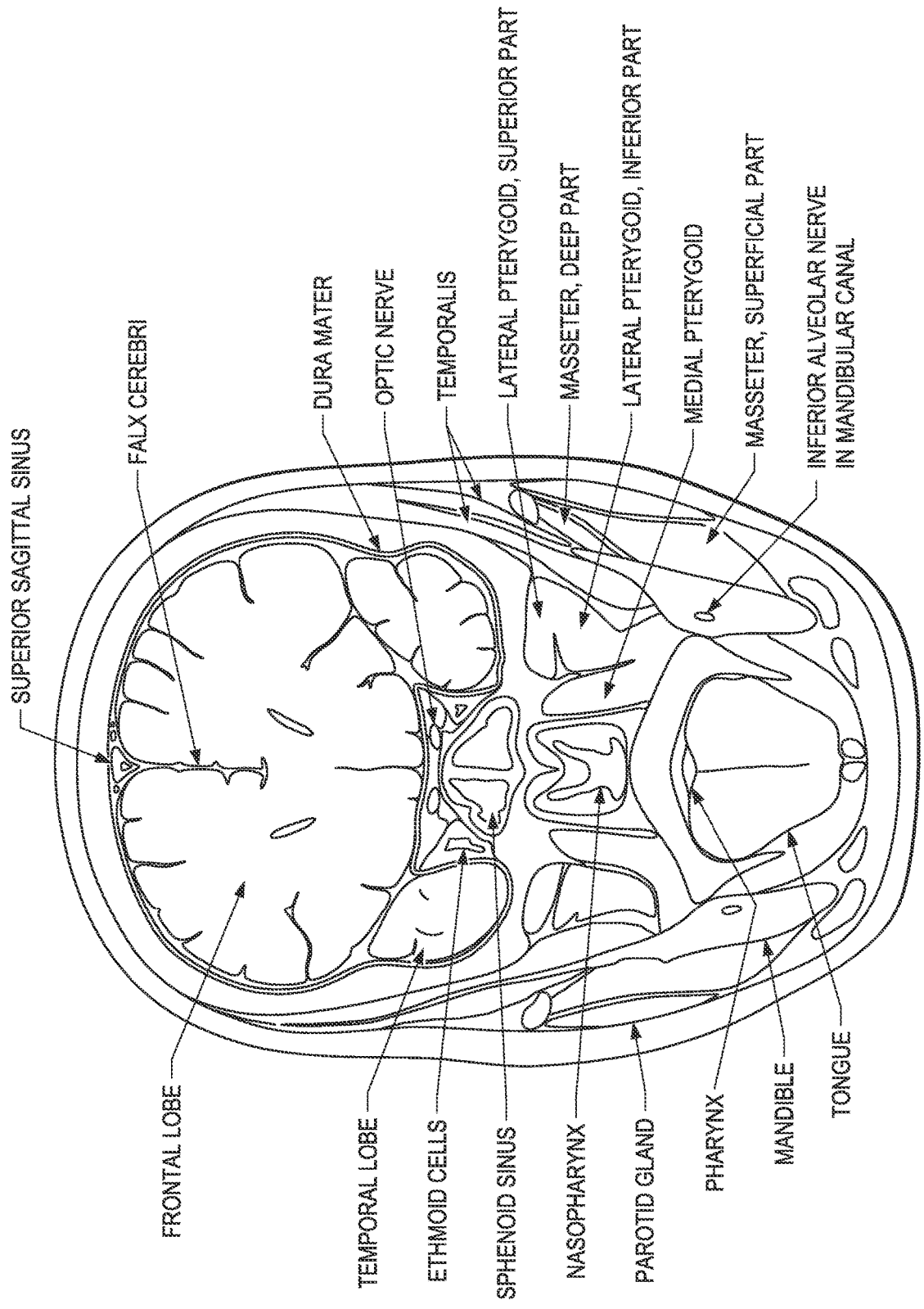
FIG. 13 shows a coronal view of various cranio-facial structures of the human head.

FIG. 13 shows a coronal view of various cranio-facial structures of the human head in proximity to which a sensor according to embodiments of the disclosure may be coupled. These include the superior sagittal sinus; the falx cerebri; the dura mater; the optic nerve; the temporalis; the superior and inferior parts of the lateral pterygoid; the superficial and deep parts of the masseter; the medial pterygoid; the inferior alveolar nerve in the mandibular canal; the tongue; the mandible; the pharynx; the parotid gland; the nasopharynx; the sphenoid sinus; the ethmoid cells; the temporal lobe of the brain; and the frontal lobe of the brain.

Figure 14:
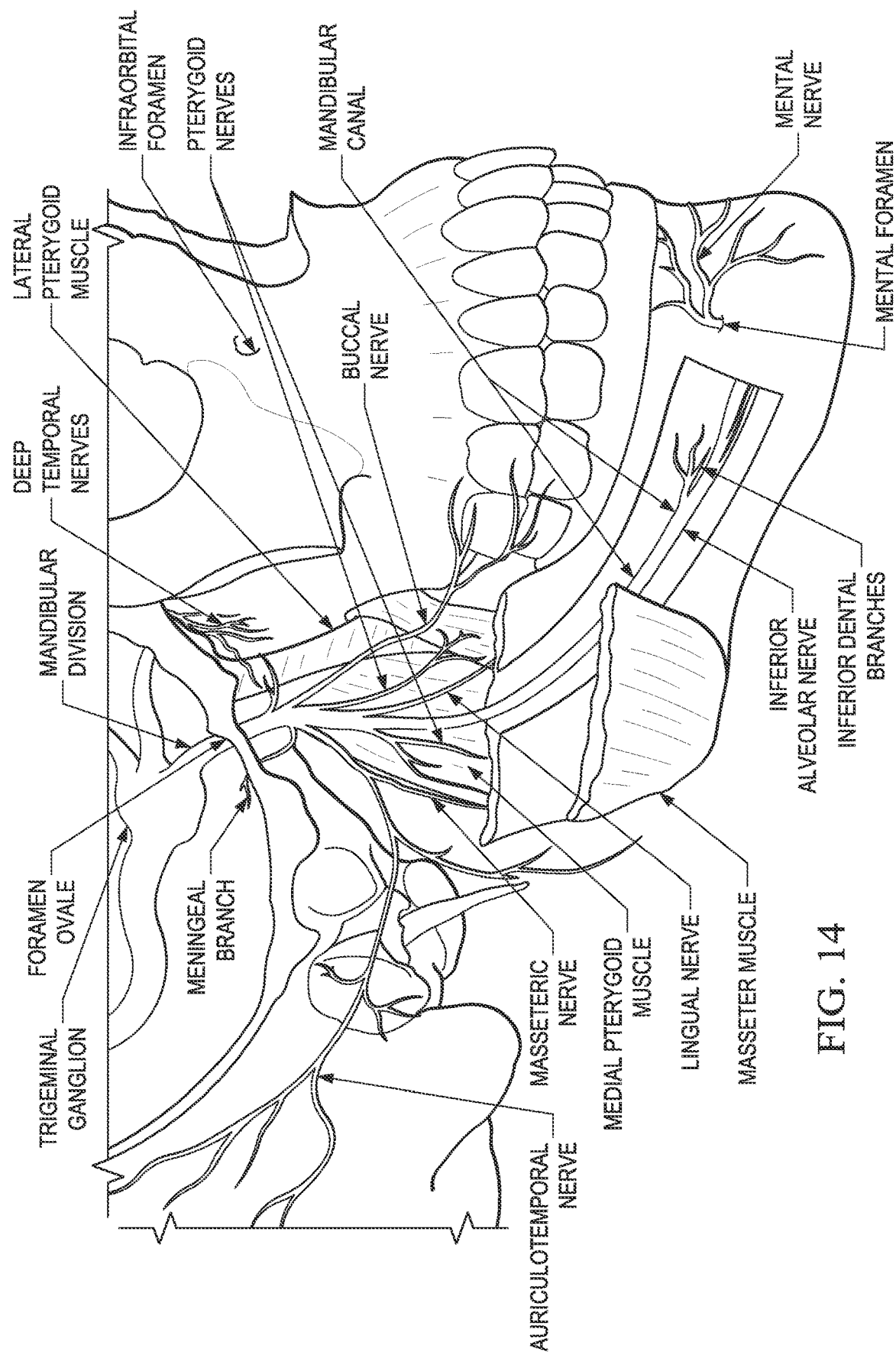
FIG. 14 shows a lateral view of various cranio-facial structures of the human head.

FIG. 14 shows a lateral view of various cranio-facial structures of the human head in proximity to which a sensor according to embodiments of the disclosure may be coupled. These include the trigeminal ganglion; the foramen *ovale*; the meningeal branch; the mandibular division; the deep temporal nerves; the lateral pterygoid muscle; the infraorbital foramen; the pterygoid nerves; the buccal nerve; the mandibular canal; the mental nerve; the mental foramen; the inferior dental branches; the inferior alveolar nerve; the masseter muscle; the lingual nerve; the medial pterygoid muscle; the masseteric nerve; and the auriculotemporal nerve.

Figure 15B:
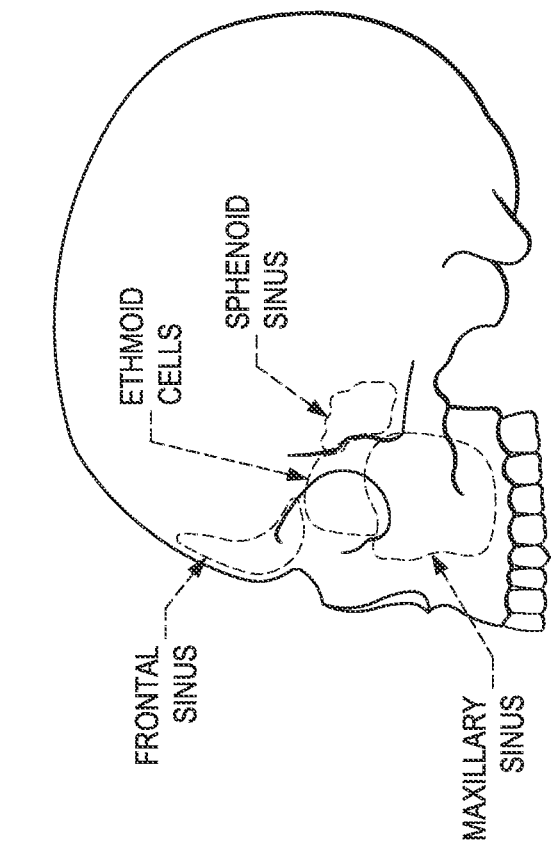
FIG. 15B shows a lateral view of cranio-facial sinuses of the human skull.
Figure 15A:
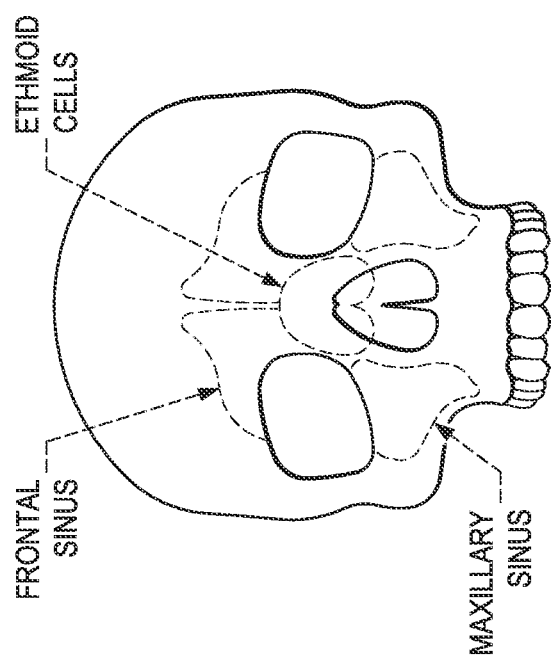
FIG. 15A shows a frontal view of cranio-facial sinuses of the human skull.

FIG. 15A shows a frontal view, and FIG. 15B shows a lateral view, of cranio-facial sinuses of the human skull in proximity to which a sensor according to embodiments of the disclosure may be coupled. These include the frontal sinus, the ethmoid cells; the sphenoid sinus; and the maxillary sinus.

Figure 16:
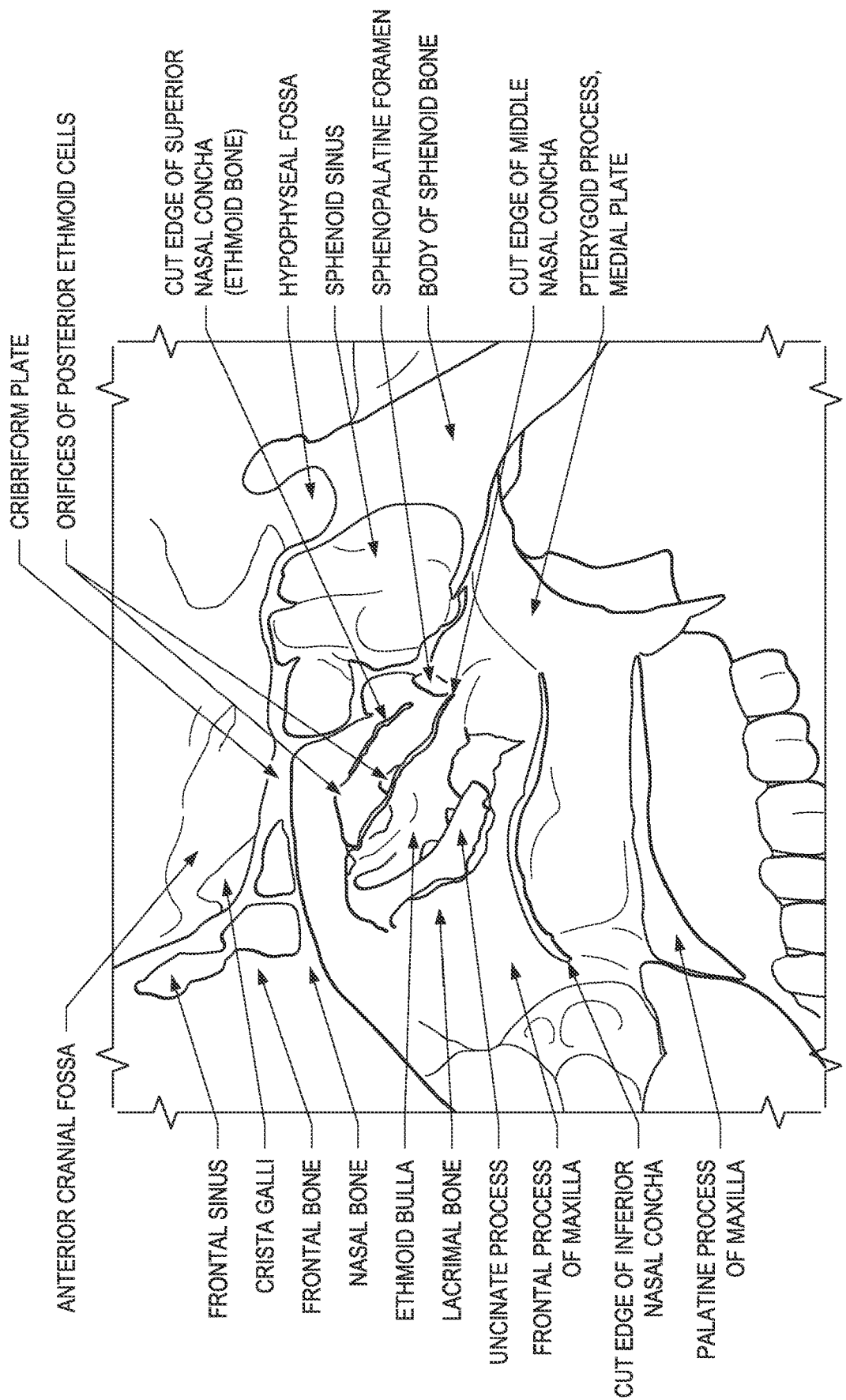
FIG. 16 shows a medial view of various cranio-facial structures of the human head.

FIG. 16 shows a medial view of various cranio-facial structures of the human head in proximity to which a sensor according to embodiments of the disclosure may be coupled. These include the anterior cranial fossa, the cribriform plate; the orifices of the posterior ethmoid cells; the cut edge of the superior nasal concha of the ethmoid bone; the hypophyseal fossa; the sphenoid sinus; the sphenopalatine foramen; the body of the sphenoid bone; the cut edge of the middle nasal concha; the medial plate of the pterygoid process; the palatine and frontal processes of the maxilla; the cut edge of the inferior nasal concha; the uncinate process; the lacrimal bone; the ethmoid bulla; the nasal bone; the frontal bone; the cristal galli; and the frontal sinus.

Figure 17A:
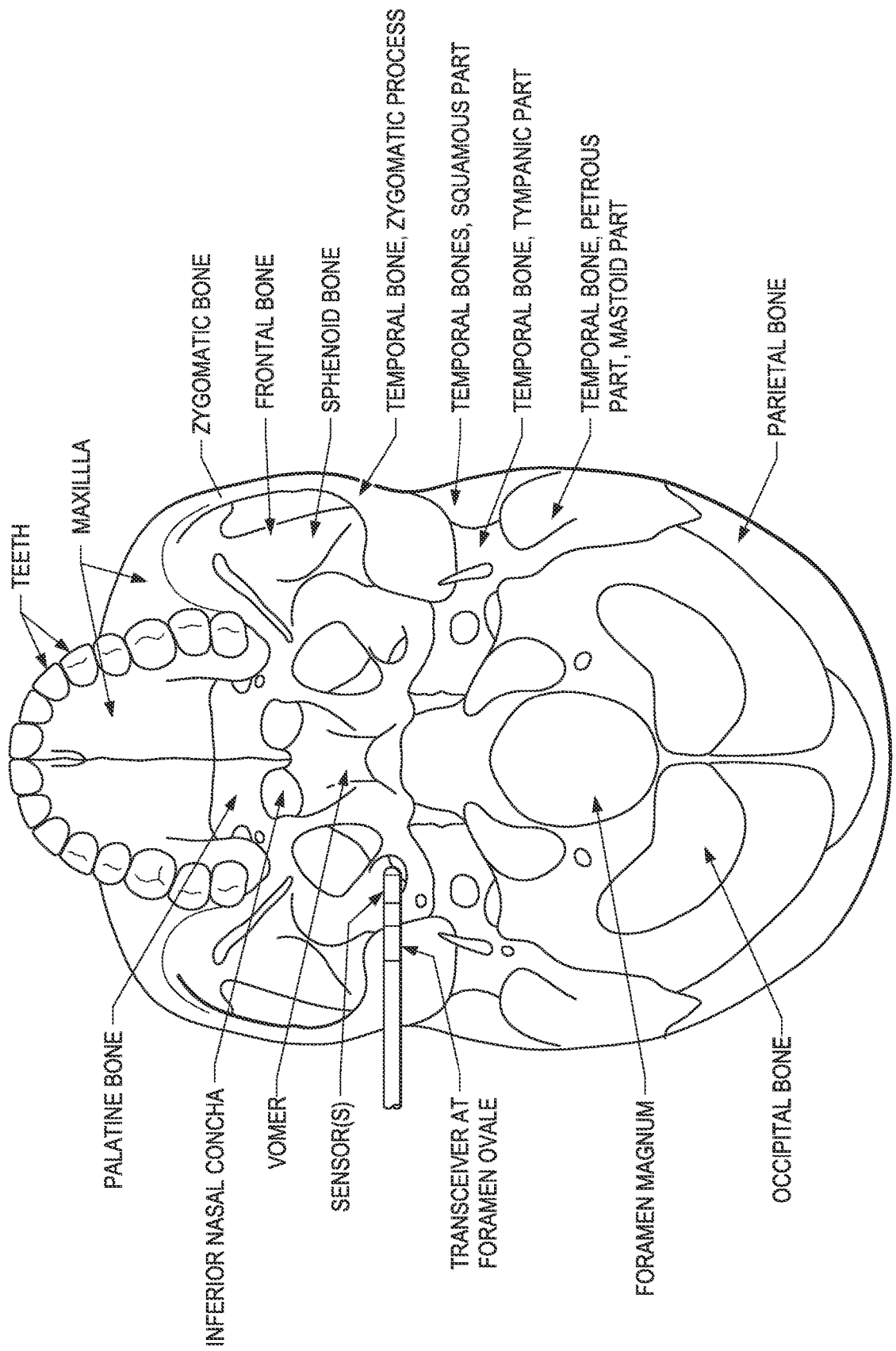
FIG. 17A shows exemplary sensor placements in proximity to the foramen *ovale* (basal view of skull), in accordance with embodiments of the present disclosure.

FIGS. 17A and 17B show exemplary sensor placements in proximity to anatomical features of the base of the human skull. The basal view of FIG. 17A shows a number of anatomical features previously mentioned in regard to FIG. 10. In addition, it identifies the frontal bone; the sphenoid bone; the zygomatic process, the squamous and tympanic parts, and the petrous and mastoid parts of the temporal bone; the occipital bone; and the inferior nasal concha.

FIG. 17A shows placement of a sensor and transceiver via a cannula to a position in proximity to the foramen *ovale*. In this depicted embodiment, the placement is made through facial structures below the skull base. Particular details of exemplary sensors, transceivers, and cannulas are presented supra.

The lateral view of FIG. 17B shows the cavernous sinus, the middle cranial fossa, the carotid canal, the petrous part of the temporal bone, the internal carotid artery, the foramen *lacerum*, the sphenoid sinus, fibrocartilage, and the carotid artery. In this depicted embodiment, the placement is made through facial structures below the skull base. Particular details of exemplary sensors, transceivers, and cannulas are presented supra.

In view of the foregoing, in one embodiment relating to sensor placement, the first location may be selected from a cribiform plate, a foramen *rotundum*, a foramen *ovale*, an internal acoustic meatus, a jugular foramen, a hypoglossal canal, an anterior fossa rostral to the sphenoid wing, a middle fossa anterior to the Petrous pyramid, a clivus, and a foramen magnum. That said, any site (e.g., a location halfway between the foramen *ovale* and the foramen *rotundum*, or 1 cm caudal to *ovale*) on the skull base may be the first or target location, with the understanding that the site should be selected such that patient safety is not compromised.

Turning to FIG. 7, an implantable first sensor system (substantially the same as the implantable sensor system 100 described in the context of FIGS. 1A and/or 1B) and an external device 700 are schematically depicted. The system includes an implanted sensor 706 having, in addition to a sensor element, an anchor for coupling the sensor to a skull 600 and a transmitter which may be coupled, e.g., wirelessly, to the external device 700.

The external device 700 may comprise a receiver 710, which may be configured to receive biological signal data from the transmitter of implanted sensor device 706. The external device 700 may comprise a first algorithm module 720 configured to analyze the biological signal data and identify a brain state of the patient based on the biological signal data. For example, the first algorithm module 720 may be configured to identify a brain state indicative of an epileptic event.

The external device 700 may comprise a response module 730. The response module 730 may be configured to initiate a responsive action based on the brain state of the patient. For example, if the brain state is found to be indicative of an epileptic event, the response module 730 may initiate one or more of the following actions: delivering a therapy for the epileptic event; determining an efficacy of the therapy; issuing a warning for the epileptic event; or logging data associated with the event such as the time of occurrence duration, etc.

When a therapy is delivered, it may include one or more of a number of therapy modalities, as described in other patents and published patent applications assigned to Cyberonics, Inc., by Flint Hills Scientific LLC. These may include electrical, mechanical or thermal stimulation of a brain structure or a cranial nerve, delivery of a drug therapy, etc. When a warning is issued, it may be issued to the patient, a caregiver, or a medical professional. For example, the warning may allow the patient time to safely cease an activity, such as driving a car, bathing, swimming, or the like, that may be contraindicated by an epileptic event.

FIG. 7 also shows additional elements that may be included in the depicted system. For example, the depicted system may further comprise a second sensor 740. The second sensor 740 may be configured to sense at least one body data signal other than brain activity. In particular examples, the second sensor 740 may be a cardio-vascular sensor or a kinetic sensor, and may be either implanted or external.

The system depicted in FIG. 7 may further comprise a second algorithm module 750. The second algorithm module 750 may be configured to process the body data signal from the second sensor 740 to detect a seizure event based on the body data. More information regarding detection of epileptic events from sensed body signals, and determination of severity and location in the body of epileptic events, can be found in U.S. patent application Ser. No. 12/756,065, filed Apr. 7, 2010; U.S. patent application Ser. No. 12/770,562, filed Apr. 29, 2010; U.S. patent application Ser. No. 12/896,525, filed Oct. 1, 2010; U.S. patent application Ser. No. 13/040,996, filed Mar. 4, 2011; U.S. patent application Ser. No. 13/091,033, filed Apr. 20, 2011; and U.S. patent application Ser. No. 13/098,262, filed Apr. 29, 2011; all of which are hereby incorporated herein by reference in their entirety.

A detection of a seizure event by the second algorithm module 750 may cause response module 730 to initiate, modify, or terminate operations of one or more other elements of the system depicted in FIG. 7. In one embodiment, the first algorithm module 720 may be configured to analyze a biological signal (e.g., an electrical or chemical signal from the patient's brain) in response to a detection of a seizure event by the second algorithm module 750.

Response module 730 may then provide a seizure confirmation signal in response to the first algorithm module 720 detecting a seizure brain state from a biological signal in response to the second algorithm module 750 detecting a seizure event from a body signal data. In other words, elements performing operations on or with brain signal data from implanted sensor 706 may do so contingently upon a detection of a seizure event from other body signal data. Alternatively or in addition, elements performing operations on or with body signal data may do so contingently upon a detection of a seizure event from brain signal data.

Figure 8:
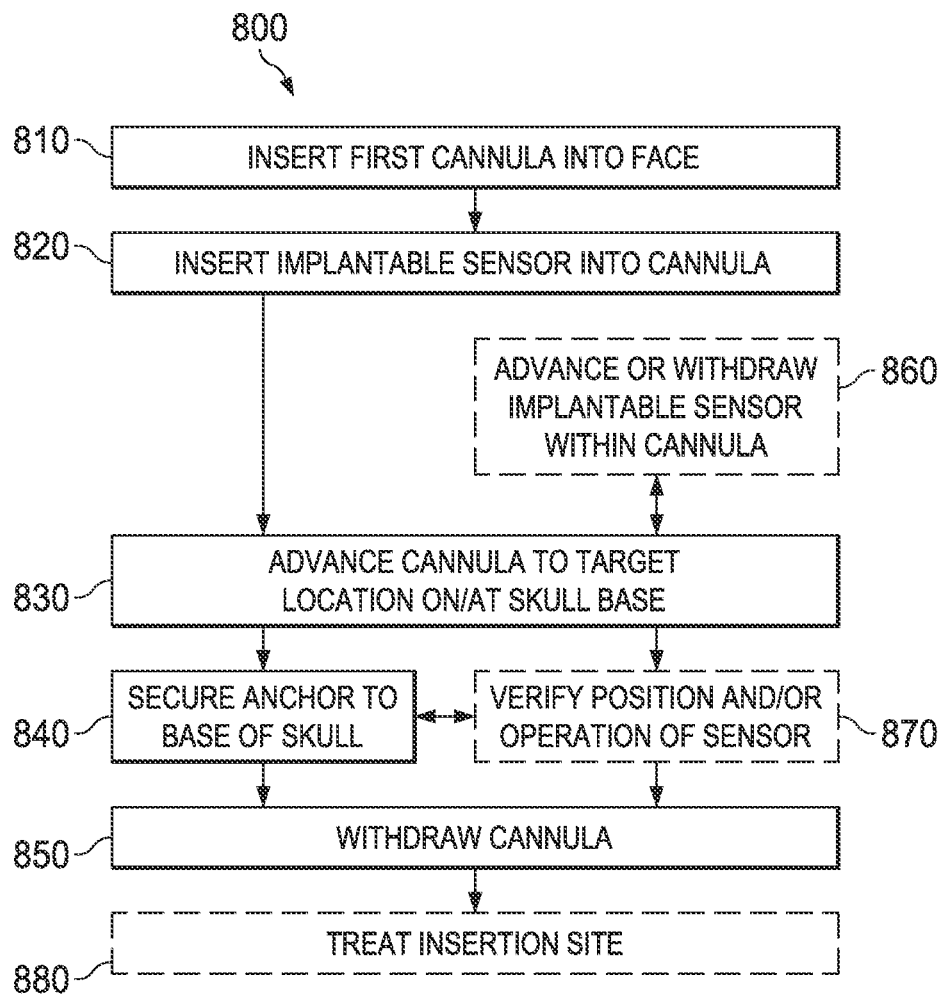
FIG. 8 presents a flowchart of a method, in accordance with one embodiment of the present disclosure.

The present disclosure also relates to methods of implanting a sensor in a patient. Turning to FIG. 8, a flowchart is presented of one such method 800.

In the depicted embodiment, the method 800 comprises inserting at 810 at least a first cannula comprising a hollow conduit through the face of the patient. By "face" is meant any portion of the patient's head at or below the skull base. That portion need not comprise the person's epidermis. For example, inserting may be performed through the oral cavity.

The method 800 also comprises inserting an implantable sensor capable of sensing at least one biological signal into the at least a first cannula (820). The implantable sensor may comprise an anchor for coupling the sensor to a patient skull base or facial bone structure; a sensing element coupled to the anchor for sensing, at a first location proximate to the patient skull base or facial bone structure, at least one biological signal of the patient, such as a brain activity signal; and a transmitter coupled to the sensor and capable of transmitting biological signal data from the sensor to an external device, as discussed supra. As should be apparent, inserting the implantable sensor into the cannula and inserting the cannula through the face of the patient could be performed in either order.

The method 800 also comprises advancing at 830 the cannula to a target location on, at, or near the base of the patient's skull base. Advancing at 830 may comprise moving the at least a first cannula to the target location. Optionally, the method 800 may further comprise adjusting 860 the position of the implantable sensor within the at least a first cannula.

The method 800 also comprises securing at 840 the anchor to the base of the skull or a facial bone proximate the first location. For example, in embodiments such as those shown in FIGS. 4A-5C, the anchor may be secured at 840 by propelling the sensor in a direction perpendicular to the axis of the cannula assembly, such as by use of a spring, a sensor advancement screw, or the like.

When the implantable sensor is at the first or target location, either before or after securing the anchor to the skull or facial bone structure (840), the method 800 may further comprise verifying at 870 at least one of a position or an operational status of the implantable sensor.

The method 800 also comprises withdrawing at 850 the at least a first cannula from the face of the patient. In embodiments where verifying at 870 is performed, withdrawing at 850 may be performed in response to said verifying.

The method 800 may further comprise treating with an anti-infection agent (e.g., an antibiotic in a topical formulation) at the site of inserting at 810, and closing the wound with appropriate means.

Figure 9:
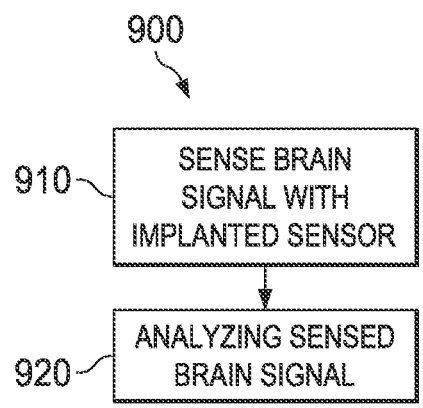
FIG. 9 presents a flowchart of a method, in accordance with one embodiment of the present disclosure.

The present disclosure also relates to methods for detecting an epileptic seizure from at least one biological signal of a patient. Turning to FIG. 9, a flowchart is presented of one such method 900.

In the depicted embodiment, the method 900 comprises sensing at 910 a biological signal (e.g., a brain electrical and/or chemical signal) with an implanted sensor at a first location proximate to a patient skull base or facial structure, wherein the implanted sensor is coupled to an anchor coupled to the skull base structure or facial bone.

The method 900 also comprises analyzing at 920 the sensed biological signal using a seizure detection algorithm to determine whether or not the patient has had an epileptic seizure. In optional further embodiments, analyzing at 920 may determine the severity of the epileptic seizure.

The present disclosure also relates to methods for monitoring cardio-vascular and/or respiration function. For example, a sensor placed through the foramen *lacerum* in close proximity to the carotid artery, such as is shown in FIG. 17B, may be used to determine one or more of blood pressure, pulse, oxygen saturation, or temperature. A sensor placed epidurally through the skull base may be used to monitor brain pressure and, indirectly, pulse and respiratory rates. One or more sensors placed close to the carotid and jugular arteries may be used to determine oxygen extraction by the brain, from which may be calculated certain metabolic parameters.

In one or more embodiments, the present disclosure relates to one or more of the following numbered paragraphs:

101. A kit for implanting a biological signal sensor in a head of a patient comprising: a sealed container having sterilized components comprising:
        at least one cannula assembly for introducing a sensor through the face of a patient, said cannula assembly comprising a piercing element, and a hollow conduit;
        an implantable sensor for sensing at least one biological signal of a patient comprising:
            an anchor for coupling the sensor to at least one skull base structure of the patient;
            at least one sensor coupled to the anchor for sensing, at a first location proximate to the at least one base skull structure of the patient, at least one biological signal of the patient;
            a transmitter coupled to the sensor and capable of transmitting data from the sensor to an external device.
    102. The kit of numbered paragraph 101, wherein the at least one cannula assembly further comprises at least one of a sensor positioning element and a sensor deployment element.

103. The kit of numbered paragraph 102, wherein the at least one sensor positioning element or sensor deployment element comprises at least one of a spring, a sensor advancement screw, or a sensor advancement gear.

104. The kit of numbered paragraph 101, wherein the cannula assembly further comprises a scout sensor for sensing at least one of the position of the cannula assembly or the proximity of the cannula assembly to at least one anatomical structure.

201. A system for sensing a biological signal of a patient comprising:
an implantable first sensor system comprising:
    an anchor for coupling the sensor to at least one patient skull base structure;
    a sensor coupled to the anchor for sensing, at a first location proximate to the at least one patient skull base structure, at least one biological signal of the patient;
    a transmitter coupled to the sensor and capable of transmitting biological signal data from the sensor to an external device;
an external device comprising:
    a receiver for receiving the biological signal data from the transmitter;
    a first algorithm module for analyzing the biological signal data to identify a brain state
    change of the patient based on the biological signal data; and
    a response module for initiating an action based on the brain state change of the patient.

202. The system of numbered paragraph 201, further comprising:
a second sensor for sensing at least one body data signal other than the biological signal; and
a second algorithm module for processing the body data signal from the second sensor to detect a seizure event based on the body data;
wherein the first algorithm module is configured to initiate analyzing the biological signal in response to a detection of a seizure event by the second algorithm module.

203. The system of numbered paragraph 201, wherein the response module initiates a seizure confirmation signal in response to the first algorithm detecting a seizure brain state change in response to the second algorithm module detecting a seizure event.

204. The system of numbered paragraph 201, wherein the second sensor is selected from a cardiac sensor or a kinetic sensor.

301. A method for implanting a sensor in a patient, comprising:
inserting at least a first cannula comprising a hollow conduit and a piercing element into the face of the patient,
inserting an implantable sensor capable of sensing at least one biological signal into the at least a first cannula, said implantable sensor comprising:
    an anchor for coupling the sensor to a patient skull base structure;
    a sensing element coupled to the anchor for sensing, at a deployed location proximate to the patient skull base structure, at least one biological signal of the patient;
    a transmitter coupled to the sensor and capable of transmitting biological signal data from the sensor to an external device;
advancing the implantable sensor to a deployment location below the base of the patient's skull;
deploying the sensing element to the deployed location;
securing the anchor to the base of the skull proximate the deployed location;
withdrawing the at least a first cannula.

302. The method of numbered paragraph 301, further comprising adjusting the position of said implantable sensor within said at least a first cannula.

303. The method of numbered paragraph 301, further comprising verifying at least one of a position or an operational status of the implantable sensor, and wherein said withdrawing is performed in response to said verifying.

401. A method for detecting an epileptic seizure from at least one biological signal of a patient, comprising:
sensing a biological signal with an implanted sensor at a first location proximate to a patient skull base structure, wherein said implanted sensor is coupled to an anchor coupled to the skull base structure;
analyzing the sensed biological signal using a seizure detection algorithm to determine whether or not the patient has had an epileptic seizure.

All of the methods and apparatuses disclosed and claimed herein may be made and executed without undue experimentation in light of the present disclosure. While the methods and apparatus of this disclosure have been described in terms of particular embodiments, it will be apparent to those skilled in the art that variations may be applied to the methods and apparatus and in the steps, or in the sequence of steps, of the method described herein without departing from the concept, spirit, and scope of the disclosure, as defined by the appended claims.

The particular embodiments disclosed above are illustrative only as the disclosure may be modified and practiced in different but equivalent manners apparent to those skilled in the art having the benefit of the teachings herein. Furthermore, no limitations are intended to the details of construction or design herein shown other than as described in the claims below. It is, therefore, evident that the particular embodiments disclosed above may be altered or modified and all such variations are considered within the scope and spirit of the disclosure. Accordingly, the protection sought herein is as set forth in the claims below.

What is claimed is:

1. A method for implanting an implantable sensor system for sensing biological signal of a patient, the method comprising:
locating in a non-contact position relative to the patient's brain tissue the implantable sensor system, the implantable sensor system including a housing, the housing including an anchor and a first sensor, the housing enclosing the first sensor, the housing coupled via a conductor in a conduit to a transmitter and a power supply, where the transmitter, the anchor, and the power supply are external to the housing and the first sensor is internal to the housing, the conductor starting at a location inside the housing and ending at a location inside the conduit and outside the housing, the anchor configured to directly couple the housing to a skull-base structure location of the patient where an anchoring location is a natural opening of a skull, the first sensor being configured to sense at least a first biological signal of the patient; and
wherein the transmitter is coupled to the first sensor and is capable of transmitting data from the first sensor to a device.

2. The method of claim 1, wherein the implantable sensor system further comprising a second sensor for sensing at least a second biological signal of the patient.

3. The method of claim 2, wherein the at least the first biological signal is selected from a first group consisting of a pulse rate, a blood pressure, a respiratory rate, a blood oxygen saturation and the at least the second biological signal is selected from a second group consisting of a velocity, an amplitude, or a direction of movement.

4. The method of claim 1, wherein the anchor comprises a grooved connection.

5. The method of claim 1, wherein the anchor comprises at least one of a threaded portion and a barbed portion.

6. The method of claim 1, wherein the power supply is configured to provide power for at least one of the transmitter or the first sensor.

7. The method of claim 6, wherein the power supply is rechargeable.

8. The method of claim 1, wherein the implantable sensor system further comprising a circuit which is configured to process an electrical signal received from the first sensor prior to a transmission of a signal by the transmitter.

9. The method of claim 8, wherein the circuit comprises an integrated circuit having at least one of an electrical filter, an amplifier, a digital-to-analog converter, and an analog-to-digital converter.

10. The method of claim 1, wherein the anchoring location for the implantable sensor system is selected from a foramen underlying a brain and a foramen through which a cranial nerve passes or a cerebral-blood vessel courses.

11. The method of claim 1, wherein the implantable sensor system further comprising an amplifier and a signal processor.

12. The method of claim 1, wherein the implanting is via a cannula.

13. The method of claim 12, wherein the implant location is a foramen *oval*.

* * * * *